US010928622B2

(12) United States Patent
Sugie et al.

(10) Patent No.: US 10,928,622 B2
(45) Date of Patent: *Feb. 23, 2021

(54) MEDICAL IMAGE PROCESSING APPARATUS, MEDICAL IMAGE PROCESSING METHOD, AND MEDICAL OBSERVATION SYSTEM

(71) Applicant: Sony Corporation, Tokyo (JP)

(72) Inventors: Yuki Sugie, Kanagawa (JP); Hisakazu Shiraki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,630

(22) Filed: Jun. 20, 2019

(65) Prior Publication Data

US 2019/0302442 A1 Oct. 3, 2019

Related U.S. Application Data

(63) Continuation of application No. 15/559,602, filed as application No. PCT/JP2016/002696 on Jun. 3, 2016.

(30) Foreign Application Priority Data

Jun. 19, 2015 (JP) ................................ 2015-124005

(51) Int. Cl.
*G06K 9/00* (2006.01)
*G02B 21/36* (2006.01)
(Continued)

(52) U.S. Cl.
CPC ....... *G02B 21/367* (2013.01); *G02B 27/0075* (2013.01); *H04N 5/2356* (2013.01);
(Continued)

(58) Field of Classification Search
CPC combination set(s) only.
See application file for complete search history.

(56) References Cited

U.S. PATENT DOCUMENTS 5,282,045 A 1/1994 Mimura et al.
5,995,668 A * 11/1999 Corset .................. G06T 9/20
382/233

(Continued)

FOREIGN PATENT DOCUMENTS

CN 1934854 A 3/2007
CN 103460684 A 12/2013
(Continued)

OTHER PUBLICATIONS

International Search Report dated Aug. 30, 2016 in PCT/JP2016/002696.

(Continued)

*Primary Examiner* — Alex Kok S Liew
(74) *Attorney, Agent, or Firm* — Xsensus LLP

(57) ABSTRACT

A medical observation system including a medical imaging device that captures a plurality of images of a living body while changing a focus position, and circuitry that generates a composite image by compositing the plurality of images captured by the medical imaging device, and switches output between the generated composite image and one of the plurality of images based on a result of analysis performed on at least one of the plurality of images.

17 Claims, 17 Drawing Sheets

(51) Int. Cl.
  *G02B 27/00*  (2006.01)
  *H04N 5/232*  (2006.01)
  *H04N 5/235*  (2006.01)
  *A61B 1/00*  (2006.01)
  *A61B 1/04*  (2006.01)
  *A61B 1/06*  (2006.01)

(52) U.S. Cl.
  CPC ..... *H04N 5/23212* (2013.01); *H04N 5/23254* (2013.01); *H04N 5/23267* (2013.01); *H04N 5/23293* (2013.01); *H04N 5/232123* (2018.08); *H04N 5/232133* (2018.08); *A61B 1/00188* (2013.01); *A61B 1/04* (2013.01); *A61B 1/0684* (2013.01)

(56) References Cited

U.S. PATENT DOCUMENTS

| | | | |
|---|---|---|---|
| 2002/0071048 | A1 | 6/2002 | Kaneda |
| 2003/0112507 | A1 | 6/2003 | Divelbiss et al. |
| 2003/0179915 | A1 | 9/2003 | Goto |
| 2003/0214706 | A1* | 11/2003 | Maddison ............ G02B 21/244 359/368 |
| 2005/0002587 | A1* | 1/2005 | Yoneyama ......... G06K 9/00127 382/254 |
| 2006/0104523 | A1 | 5/2006 | Suzuki |
| 2007/0203394 | A1 | 8/2007 | Wiklof |
| 2008/0259176 | A1 | 10/2008 | Tamaru |
| 2011/0245660 | A1* | 10/2011 | Miyamoto ............. A61B 6/032 600/424 |
| 2012/0218516 | A1 | 8/2012 | Imamura |
| 2013/0090554 | A1 | 4/2013 | Zvuloni et al. |
| 2014/0210957 | A1* | 7/2014 | Kodama ................ G03B 13/36 348/50 |
| 2014/0333790 | A1* | 11/2014 | Wakazono ......... H04N 5/23241 348/222.1 |

FOREIGN PATENT DOCUMENTS

| | | |
|---|---|---|
| EP | 1336888 A1 | 8/2003 |
| JP | 11-177873 A | 7/1999 |
| JP | 2005-099736 A | 4/2005 |
| JP | 2014-232166 A | 12/2014 |
| WO | 02/082805 A1 | 10/2002 |
| WO | 2014/083574 A2 | 6/2014 |
| WO | 2016/067425 A1 | 5/2016 |

OTHER PUBLICATIONS

Office Action dated May 9, 2019 in Japanese Patent Application No. 2015-124005.
Japanese Notification of Reason for Refusal dated Dec. 19, 2019 in Japanese Application No. 2015-124005.
Chinese First Office Action dated Nov. 28, 2019 in Chinese Application No. 2016800343210.

* cited by examiner

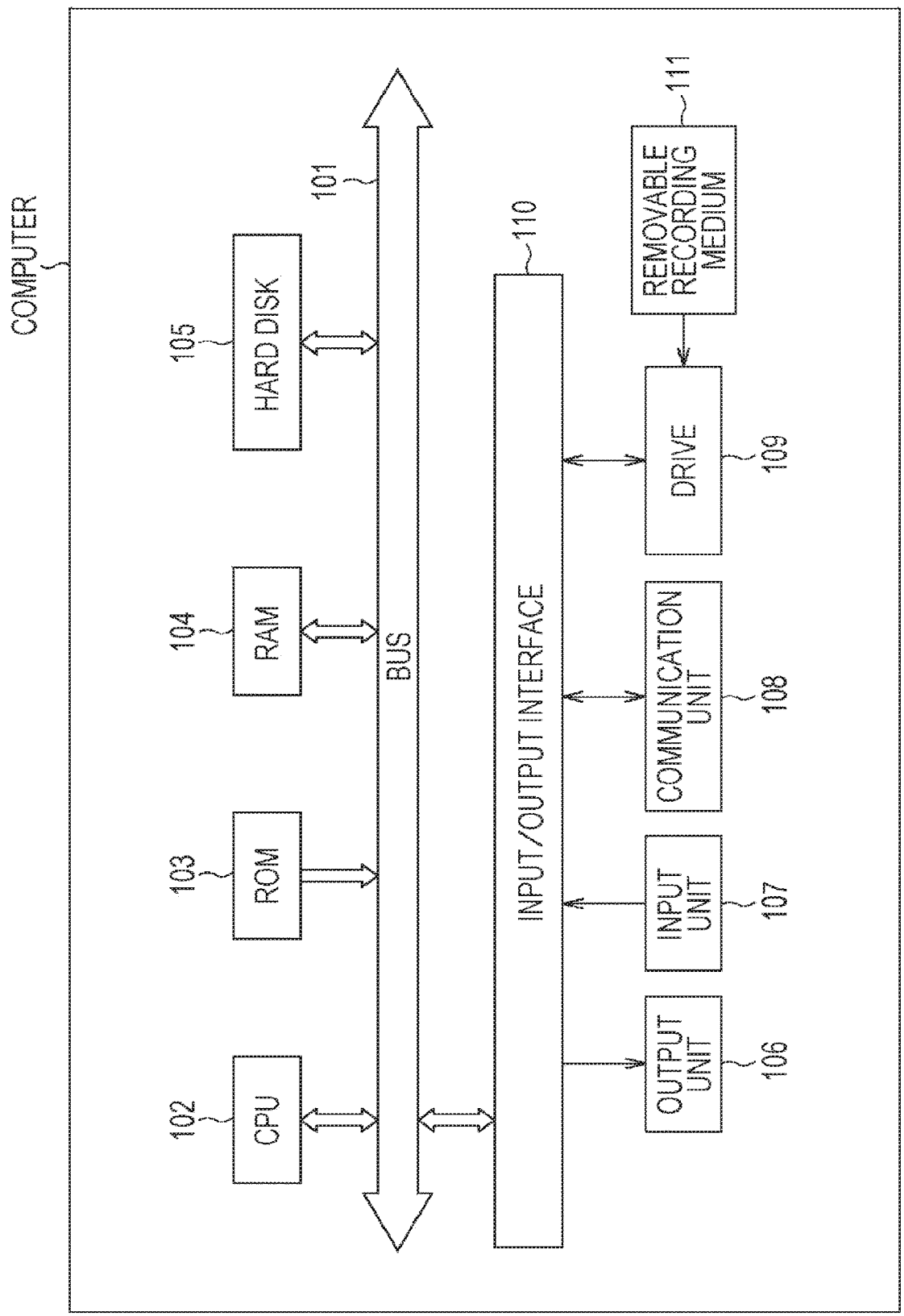

MEDICAL IMAGE PROCESSING APPARATUS, MEDICAL IMAGE PROCESSING METHOD, AND MEDICAL OBSERVATION SYSTEM

CROSS-REFERENCE TO RELATED APPLICATIONS

This application is a continuation of U.S. application Ser. No. 15/559,602, filed Sep. 19, 2017, which is based on PCT filing PCT/JP2016/002696, filed Jun. 3, 2016, and claims priority to JP 2015-124005, filed Jun. 19, 2015, the entire contents of each are incorporated herein by reference.

TECHNICAL FIELD

The present technology relates to a medical image processing apparatus, a medical image processing method and a medical observation system, particularly to a medical image processing apparatus, a medical image processing method and a medical observation system by which a deep focus image can be obtained with a low delay and at a high frame rate, for example.

CROSS REFERENCE TO RELATED APPLICATIONS

This application claims the benefit of Japanese Priority Patent Application JP 2015-124005 filed on Jun. 19, 2015, the entire contents of which are incorporated herein by reference.

BACKGROUND ART

A depth of field of a photographed image obtained by a medical microscope or the like is shallow, where an image of an object at a slightly different depth from a focus position (focus plane) that is in locus in a real space is blurred.

In a photographed image obtained by the medical microscope in a brain surgery, for example, a frontward object is photographed in the periphery while an object (such as a surgical site) being a focus of attention located more or less at the back is photographed at the center. At this time, the object in the periphery of the photographed image is blurred when a focus is adjusted to bring the object at the center of the photographed image into focus, which may affect observability of the object and operability of the medical microscope.

Accordingly, for example, there is proposed a real-time all-in-focus microscopic camera which performs high-speed photographing of an image while changing a focus position (focal length) and obtains a deep focus image (an all-in-focus image) from a plurality of images obtained by the photographing (refer to Patent Literature 1, for example).

CITATION LIST

Patent Literature

PTL 1: International Publication No. WO 2002/082805

SUMMARY OF INVENTION

Technical Problem

Now, when an image is to be provided to a user such as a doctor performing an operation with medical equipment such as the medical microscope, it is desirable from the nature of the medical field that the image is provided with a low delay and at a high frame rate.

In view of such circumstances, it is desirable to be able to obtain a deep focus image with a low delay and at a high frame rate.

Solution to Problem

A medical image processing apparatus according to an embodiment of the present technology includes circuitry configured to generate a composite image by compositing a plurality of images obtained by capturing with a medical imaging device a living body while changing a focus position, and switch output between the generated composite image and one of the plurality of images based on a result of analysis performed on at least one of the plurality of images.

A medical image processing method according to an embodiment of the present technology includes generating a composite image by compositing a plurality of images obtained by capturing with a medical imaging device a living body while changing a focus position, and switching output between the generated composite image and one of the plurality of images based on a result of analysis performed on at least one of the plurality of images A medical observation system according to an embodiment of the present technology includes a medical imaging device configured to capture a plurality of images of a living body while changing a focus position, and circuitry configured to generate a composite image by compositing the plurality of images captured by the medical imaging device, and switch output between the generated composite image and one of the plurality of images based on a result of analysis performed on at least one of the plurality of images.

Note that the medical image processing apparatus and the medical observation system may be independent apparatus and system or an internal block making up a single apparatus.

Advantageous Effects of Invention

According to an embodiment of the preset technology, the deep focus image can be obtained with the low delay and at the high frame rate, for example.

Note that the effect is not limited to the one described above but may be any effect described in the present disclosure.

BRIEF DESCRIPTION OF DRAWINGS

FIG. 17 is a block diagram illustrating a configuration example of an embodiment of a computer to which the present technology is applied.

DESCRIPTION OF EMBODIMENTS

Embodiment of Medical Observation System to Which Present Technology is Applied

Figure 1:
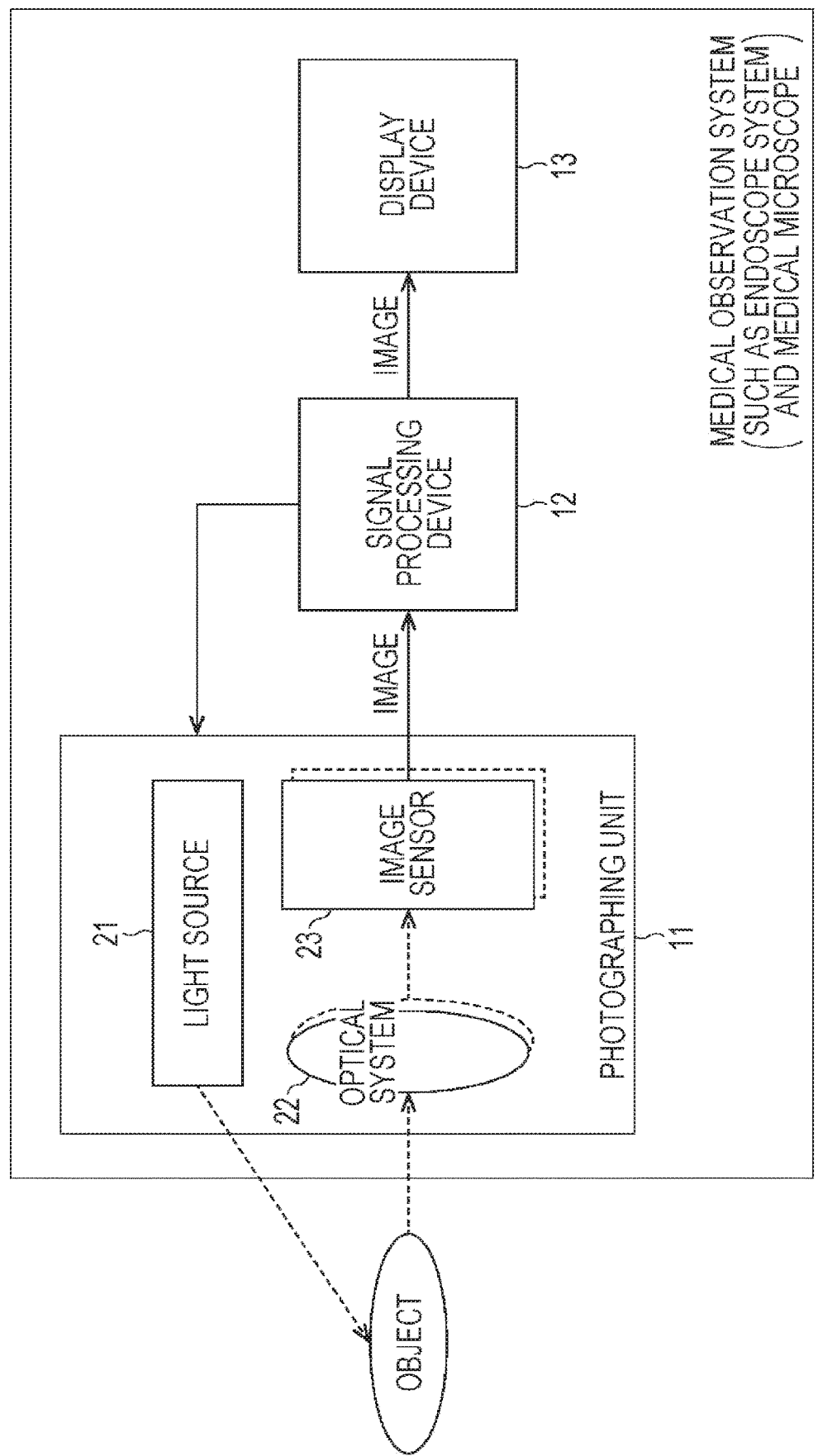
FIG. 1 is a block diagram illustrating a configuration example of an embodiment of a medical observation system to which the present technology is applied.

FIG. 1 is a block diagram illustrating a configuration example of an embodiment of a medical observation system to which the present technology is applied.

The medical observation system illustrated in FIG. 1 can be applied to medical equipment such as a medical endoscope system or a medical electron microscope (surgical microscope) that has a function of observing a living body.

As illustrated in FIG. 1, the medical observation system includes a photographing unit 11, a signal processing device 12, and a display device 13.

The photographing unit 11 illuminates and photographs an object being a living body such as a surgical site of a human body subjected to an operation, for example, and supplies a photographed image being an image of the living body obtained by the photographing to the signal processing device 12.

The photographing unit 11 includes a light source 21, art optical system 22 and an image sensor 23.

The light source 21 is formed of a Light Emitting Diode (LED) or the like and emits light illuminating the object.

The optical system 22 is provided in a lens barrel (not shown) and formed of optical components such as a focus lens and a diaphragm. The optical system 22 condenses object light (reflected light) that is the light emitted from the light source 21, reflected off of the object and incident on the optical system onto the image sensor 23.

The image sensor 23 is a Complementary Metal Oxide Semiconductor (CMOS) sensor, for example, which receives the object light from the optical system 22, performs photoelectric conversion and photographs the object. A photographed image of the object photographed by the image sensor 23 is supplied to the signal processing device 12.

Note that the photographing unit 11 can photograph, as the photographed image, a two-dimension (2D) image and a 3D image formed of a left eye image (Left (L) image) and a right eye image (Right (R) image).

When photographing the 3D image, the photographing unit 11 is provided with the optical system 22 and the image sensor 23 used to photograph the L image, and the optical system 22 and the image sensor 23 used to photograph the R image as indicated with a dotted line in the drawing.

Moreover, when the photographing unit 11 photographs the 3D image, the signal processing device 12 performs similar processing on each of the L image and the R image, for example.

In order to simplify description, it is hereinafter assumed that the photographing unit 11 photographs the 2D image as the photographed image.

The signal processing device 12 performs appropriate signal processing on the photographed image obtained from the photographing unit 11 and supplies an image obtained as a result of the signal processing to the display device 13.

In addition, the signal processing device 12 controls the photographing unit 11 as appropriate.

Specifically, the signal processing device 12 controls the light source 21 to control intensity of the illumination provided by the light source 21, for example. The signal processing device 12 also controls the optical system 22 to adjust the diaphragm, a focus (position) and a zoom, for example. Moreover, the signal processing device 12 controls the image sensor 23 to control a frame rate of a photographed image and exposure lime (shutter speed) in photographing to obtain a photographed image, for example.

The display device 13 displays the image supplied from the signal processing device 12. The display device 13 can be a display integral with the signal processing device 12, a stationary display provided separately from the signal processing device 12, or a head mount display, for example.

First Configuration Example of Signal Processing Device 12

Figure 2:
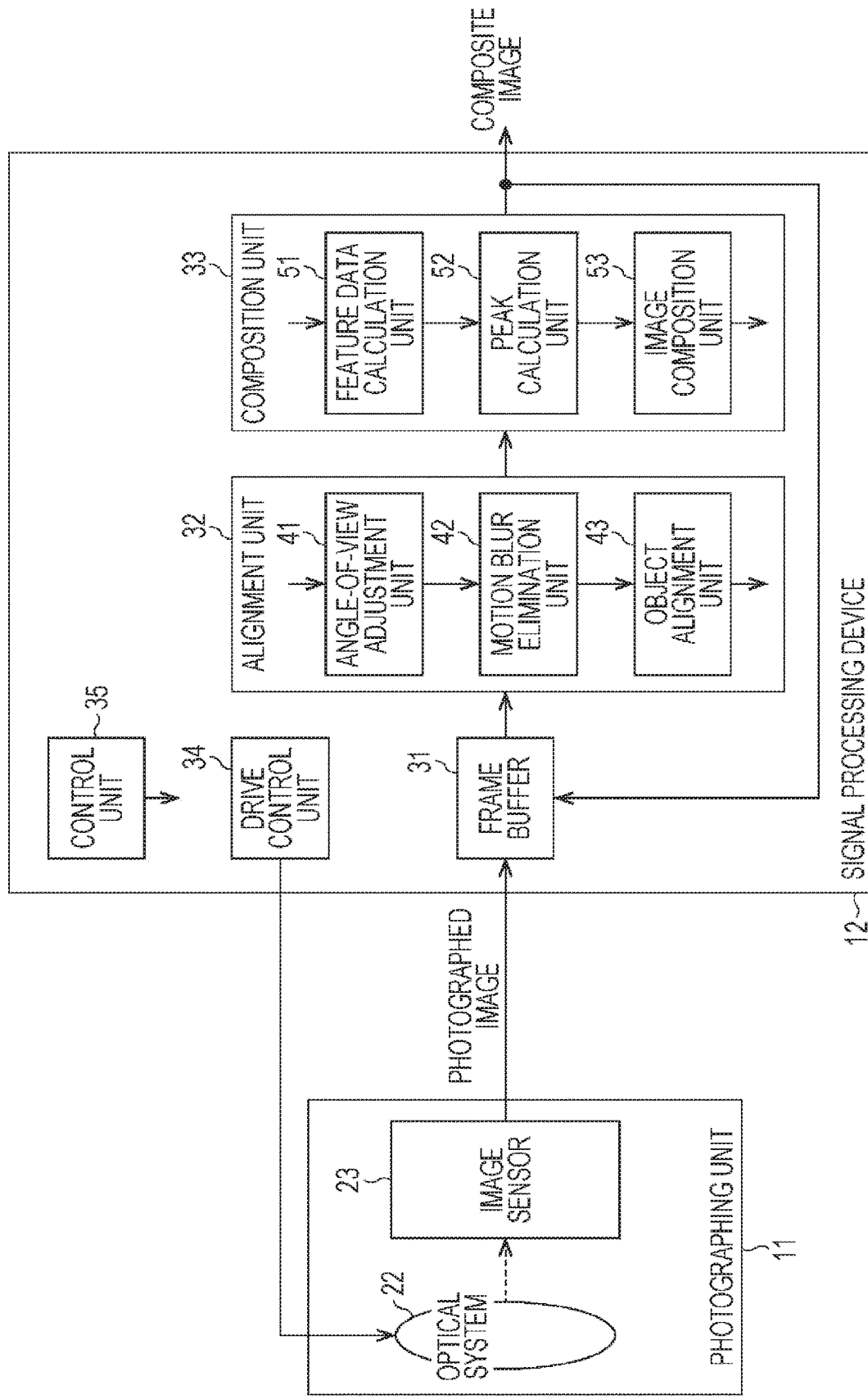
FIG. 2 is a block diagram illustrating a first configuration example of a signal processing device 12.

FIG. 2 is a block diagram illustrating a first configuration example of the signal processing device 12 in FIG. 1.

As illustrated in FIG. 2, the signal processing device 12 includes a frame buffer 31, an alignment unit 32, a composition unit 33, a drive control unit 34 and a control unit 35. A photographed image from the photographing unit 11 (specifically the image sensor 23 thereof) and a composite image (to be described) from the composition unit 33 are supplied to the frame buffer 31.

The frame buffer 31 temporarily stores the photographed image from the photographing unit 11 and the composite image from the composition unit 33.

Here, the photographing unit 11 performs (high-speed) photographing at a frame rate higher than or equal to a frame rate of the image displayed in the display device 13 to obtain the photographed image while changing a focus position with the optical system 22 controlled by the drive control unit 34 to be described.

As a result, a plurality of photographed images with different focus positions is supplied from the photographing unit 11 to the frame buffer 31, which stores these plurality of photographed images with different focus positions.

The alignment unit 32 performs alignment between the last composite image and the latest photographed image stored in the frame buffer 31 and supplies the aligned composite image and photographed image to the composition unit 33.

Specifically, the alignment unit 32 includes an angle-of-view adjustment unit 41, a motion blur elimination unit 42, and an object alignment unit 43.

The angle-of-view adjustment unit 41 adjusts an angle of view of each of the composite image and the photographed image, and supplies the composite image and the photographed image after adjusting the angle of view thereof to the motion blur elimination unit 42.

The motion blur elimination unit 42 eliminates motion blur in the photographed image supplied from the angle-of-view adjustment unit 41, and supplies the photographed image from which the motion blur is eliminated to the object alignment unit 43 along with the composite image.

The object alignment unit 43 detects motion in the composite image and the photographed image supplied from the motion blur elimination unit 42 and, on the basis of a result of the motion detection, performs alignment between the composite image and the photographed image.

In other words, the object alignment unit 43 performs alignment to align the position of an object in the composite image with the same object in the photographed image.

The object alignment unit 43 then supplies the aligned composite image and photographed image to the composition unit 33.

The composition unit 33 generates a latest composite image by compositing the composite image and the photographed image supplied from the alignment unit 32 (specifically the object alignment unit 43 thereof).

Specifically, the composition unit 33 includes a feature data calculation unit 51, a peak calculation unit 52 and an image composition unit 53.

The feature data calculation unit 51 calculates feature data (hereinafter also referred to as in-focus feature data) representing a degree of focus (being in focus) for a pixel in each of the composite image and the photographed image supplied from the alignment unit 32, and supplies the in-focus feature data to the peak calculation unit 52.

The peak calculation unit 52 calculates a peak of the in-focus feature data of the pixel arranged at the same position in each of the composite image and the photographed image. That is, the peak calculation unit 52 detects the larger in-focus feature data between the in-focus feature data of the pixel arranged at the same position in each of the composite image mid the photographed image, and supplies a detected result (hereinafter also referred to as a detected peak) to the image composition unit 53.

The image composition unit 53 generates the latest composite image by compositing the composite image and the photographed image supplied from die alignment unit 32 in accordance with the detected peak supplied from the peak calculation unit 52.

The (latest) composite image obtained in the image composition unit 53 is supplied to the frame buffer 31 and also output to the display device 13 (FIG. 1) as appropriate.

The drive control unit 34 drives the optical system 22 to shift the focus position.

The control unit 35 controls the entire signal processing device 12.

Figure 3:
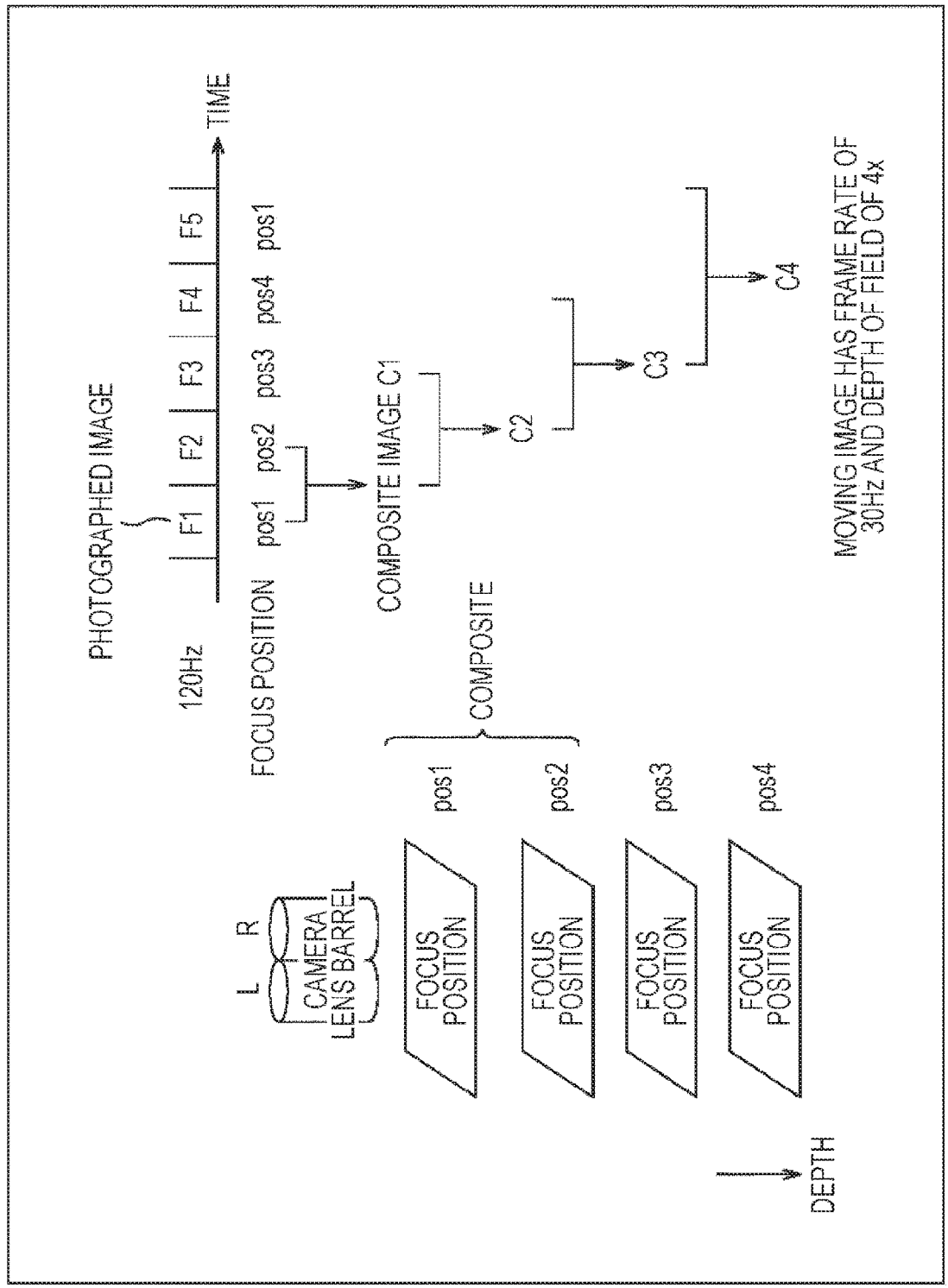
FIG. 3 is a diagram illustrating an overview of photographing performed to obtain a photographed image in a photographing unit 11 and generating a composite image in the signal processing device 12.

Overview of Photographing Performed to Obtain Photographed Image and Generating Composite Image FIG. 3 is a diagram illustrating an overview of photographing performed to obtain the photographed image in the photographing unit 11 and generating the composite image in the signal processing device 12.

FIG. 3 illustrates an example where the photographing unit 11 performs photographing to obtain photographed image (frames) F1, F2, F3 and the like at the frame rate of 120 Hz.

Moreover, as illustrated in FIG. 3, the focus position in obtaining the photographed image is periodically shifted to four focus positions pos1, pos2, pos3 and pos4 in each frame.

Here, the focus positions pos1, pos2, pos3 and pos4 are different and have relationship represented by expression pos1<pos2<pos3<pos4 in FIG. 3.

The photographing unit 11 performs photographing to obtain the photographed images F1, F2, F3 and the like while periodically changing the focus position to the focus positions pos1, pos2, pos3, and pos4 as described above.

As a result, the photographed image F1 is an image at the focus position pos1 (image focused on the focus position pos1), the photographed image F2 is an image at the focus position pos2, the photographed image F3 is an image at the focus position pos3, and a photographed image F4 is an image at the focus position pos4.

A photographed image F5 is an image focused on the focus position pos1 and, in this manner, a photographed image from then on corresponds to an image focused on a focus position that changes periodically.

The signal processing device 12 theoretically generates a deep focus composite image by compositing a plurality of photographed images with different focus positions such as four frames of photographed images focused on the focus positions pos1, pos2, pos3, and pos4.

A first composition method and a second composition method can be adopted, for example, as an Extended Depth of Field (EDoF) method that generates the deep focus composite image by compositing the plurality of photographed images with different focus positions such as the photographed images focused on the focus positions pos1, pos2, pos3, and pos4.

In the first composition method, the photographed image focused on each of the focus positions pos1 to pos3 is aligned with the photographed image focused on the focus position pos4 that is the latest photographed image among the photographed images focused on the focus positions pos1 to pos4.

After that, among the pixels of the photographed images focused on the focus positions pos1 to pos4 after alignment, a pixel of the photographed image focused on the focus position with the maximum (peak) in-focus feature data is selected as a pixel of a composite image, whereby a composite image formed of such pixel is generated.

In the second composition method, for example, the photographed image F1 at the focus position pos1 obtained first becomes the composite image as is. That composite image (last composite image) and the following photographed image F2 at the focus position pos2 are then composited.

In other words, the last composite image is aligned with the photographed image F2 at the focus position pos2 being the latest photographed image.

After that, between the pixels of the photographed image F2 at the focus position pos2 and the composite image after alignment, a pixel of the photographed image F2 or the composite image with the maximum (larger) in-focus feature data is selected as a pixel of a latest composite image C1, whereby the latest composite image C1 formed of such pixel is generated.

As for the photographed image B at the focus position pos3 photographed after the photographed image F2 at the focus position pos2, the composite image C1 serves as the last composite image C1, where the composite image C1 and the photographed image F3 (latest photographed image) at the focus position pos3 are composited in the similar manner to generate a latest composite image C2.

As for the photographed image F4 at the focus position pos4 photographed after the photographed image F3 at the focus position pos3, the composite image C2 serves as the last composite image C2 where the composite image C2 and the photographed image F4 at the focus position pos4 are composited in the similar manner to generate a latest composite image C3.

Likewise, as for a succeeding photographed image, a latest composite image is generated by compositing the last composite image and the latest photographed image in the second composition method.

Each of the composite image obtained by compositing the photographed images at the focus positions pos1 to pos4 in the first composition method and the composite image C3 obtained by the second composition method is a deep focus image with the depth of field including the focus positions pos1 to pos4.

Moreover, in either the first or second composition method, the composite image can be obtained after the photographed images at the focus positions pos1 to pos4 are obtained.

Note that in the first composition method, the four frames of photographed images at the focus positions pos1 to pos4 are subjected to the composition processing (alignment processing performed in the alignment unit 32 and composition processing performed in the composition unit 33) that generates the composite image.

In the second composition method, on the other hand, the two frames of images including the last composite image and the latest photographed image are subjected to the composition processing.

Therefore, while there is no difference in the depth of field of the composite image obtained in the first and second composition methods, the composition processing can be performed faster in the second composition method than in the first composition method when three or more frames of photographed images are used to generate the composite image.

According to the second composition method, as described above, the composition processing can be performed faster so that the composite image being a deep focus image can be obtained with a low delay and at a high frame rate.

Now, when an image is to be provided to a user such as a doctor performing an operation with medical equipment, it is desirable from the nature of the medical field that the image is provided with a low delay and at a high frame tale as described above, in which ease the second composition method can be employed to be able to provide the deep focus image with the low delay and at the high frame rate. As a result, observability of an object (ease of observing an object) as well as ease of performing an operation on the object can be increased.

Moreover, according to the second composition method, the composition processing can be performed in a short time to be able to obtain the deep focus image promptly even when focus drive in the photographing unit 11 is slow and takes time.

Note that when the photographing unit 11 performs photographing to obtain the photographed image at the frame rate of 120 Hz while periodically changing the focus position to the focus positions pos1, pos2, pos3, and pos4 as illustrated in FIG. 3, the signal processing device 12 can generate a single frame of a composite image by compositing four frames of photographed images every time the four frames of the photographed images at the focus positions pos1, pos2, pos3, and pos4 are obtained. In this case, there can be obtained a composite image with the depth of field that is (approximately) four times that of a photographed image at a single focus position and die frame rate of 30 Hz.

Moreover, when the photographing unit 11 performs photographing to obtain the photographed image at the frame rate of 120 Hz while periodically changing the focus position to the focus positions pos1, pos2, pos3, and pos4 as illustrated in FIG. 3, the signal processing device 12 can generate a single frame of a composite image by compositing preceding four frames of the photographed images including a latest photographed image every time the latest photographed image is obtained. In this case, there can be obtained a composite image with the depth of field that is (approximately) four times that of a photographed image at a single focus position and the frame rate of 120 Hz.

While the medical observation system of FIG. 1 can adopt either the first or second composition method, there will be described an example where the second composition method between the first and second composition methods is adopted.

Processing Performed by Alignment Unit 32 and Composition Unit 33

Figure 4:
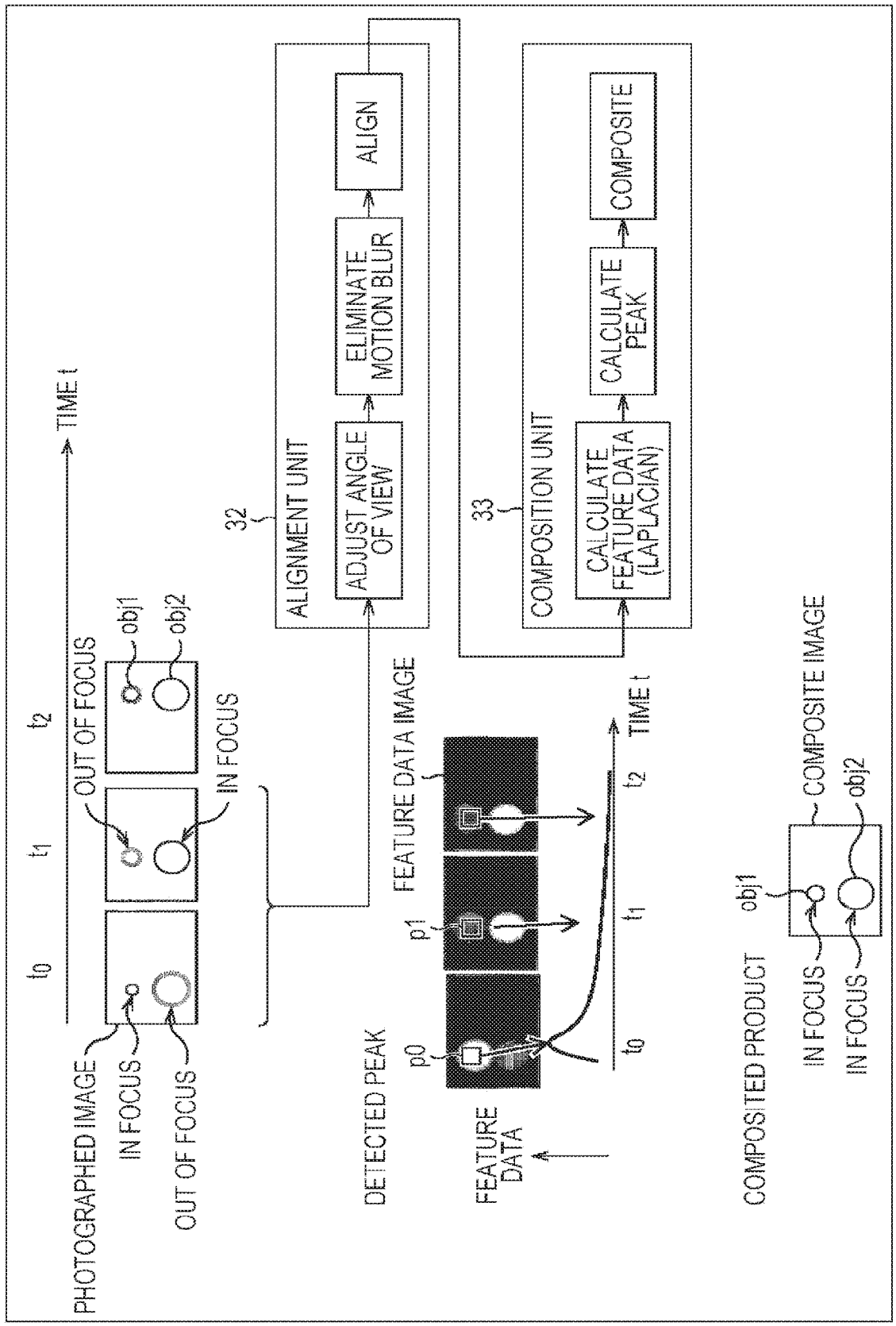
FIG. 4 is a diagram illustrating an example of processing performed by an alignment unit 32 and a composition unit 33.

FIG. 4 is a diagram illustrating an example of processing performed by five alignment unit 32 and the composition unit 33 illustrated in FIG. 2.

The photographing unit 11 performs photographing to obtain the photographed image while changing the focus position as described with reference to FIG. 3.

FIG. 4 illustrates a case where a photographed image including objects obj1 and obj2 is obtained at times t0, t1, and t2.

Focus positions of the photographed images obtained at times t0 to t2 are different so that, in the photographed image at time t0, the object obj1 is in focus while the object obj2 is out of focus. In the photographed images obtained at times t1 and t2, the object obj1 is out of focus while the object obj2 is in focus.

Here, there will be described the processing performed by the alignment unit 32 and the composition unit 33 with reference to FIG. 4 assuming that the photographed image at time t0 is the last composite image and the photographed image at time t1 is the latest photographed image, in order to simplify description.

The alignment unit 32 aligns the position of the photographed image at time t0 being the last composite image with the photographed image at time t1 being the latest photographed image.

The alignment is performed such that the identical objects in the photographed images obtained at limes t0 and t1 overlap each other as much as possible.

Specifically, the angle-of-view adjustment unit 41 of the alignment unit 32 adjusts the angle of view of the photographed image at time t1 as a composite image, for example, such that the objects obj1 as well as the objects obj2 identical in the photographed images at times t0 and t1 overlap each other as much as possible.

The angle of view is adjusted on the assumption that the photographed image at time t1 being the latest photographed image is highly correlated with the photographed image at time t0 being the last composite image, where the angle of view of the photographed image at time t0 is changed little by little to compute cross correlation or a sum total of an absolute value of a difference in pixel values as a correlation value representing correlation between the photographed images at times t0 and t1.

Then there is computed the angle of view with which the correlation value between the photographed images at times t0 and t1 is the highest, and the angle of view of the photographed image at time t0 is adjusted to such angle of view (the photographed image at time t0 is scaled up or down).

The photographed image being obtained while changing the focus position, the angle of view may vary slightly between one photographed image and a next photographed image due to the shift in the locus position. The angle of view is adjusted in order to correct such variation in the angle of view.

After adjusting the angle of view, the motion blur elimination unit 42 of the alignment unit 32 eliminates motion blur in the photographed image at time t1 being the latest photographed image.

An arbitrary method can be adopted to eliminate the motion blur. When a blur kernel can possibly be the filler causing the motion blur, for example, the motion blue can be eliminated by deconvolution of the blur kernel.

Note that the processing of eliminating the motion blur in the motion blur elimination unit 42 can be skipped. That is, the processing of eliminating the motion blur can be skipped when the motion blur is eliminated by deconvolution of the blur kernel which, however, is not be assumed as the filter causing the blur, for example.

While the motion blur is eliminated only from the latest photographed image in this case, the motion blur can also be eliminated from the last composite image. However, the motion blur is already eliminated from the last composite image since it is obtained by compositing the deburred photographed image and a composite image obtained before the last composite image except for a case where the photographed image serves as the last composite image as is. Therefore, the last composite image does not have to be subjected to elimination of the motion blur except for the ease where the photographed image serves as the last composite image as is.

The object alignment unit 43 of the alignment unit 32 thereafter aligns the position of an object in the photographed image at time t0 being the last composite image with the position of an object in the photographed image at time t1 being the latest photographed image.

The object alignment unit 43 performs alignment on the assumption that the photographed image at time t1 being the latest photographed image mid the photographed image at time t0 being the last composite image do not vary much (do not have a big difference) in the depth of field, namely, the identical object is in focus in both the photographed image at time t1 being the latest photographed image and the photographed image at time t0 being the last composite image.

The object alignment unit 43 performs alignment by detecting motion between the photographed image at time t1 being the latest photographed image and the photographed image at time t0 being the last composite image pixel by pixel, for example.

The motion detection can be performed by an arbitrary method, for example. The motion detection can be performed by block matching or a Kanade Lucas Tomasi (KLT) method bused on a feature point, for example.

In the alignment performed by the object alignment unit 43, a motion vector is detected pixel by pixel in the motion detection, and then the motion vector detected pixel by pixel is used to find one or a plurality of representative vectors representing motion from one or a plurality of points in the photographed image at lime t0 being the last composite image to one or a plurality of points in the photographed image at time t1 being the latest photographed image.

Then, a projection transformation matrix that realizes projection transformation matching the motion represented by the representative vector is computed, so that the photographed image at time t0 being the last composite image is subjected to projection transformation according to the projection transformation matrix to align the position of the photographed image at time t0 being the last composite image with the photographed image at time t1 being the latest photographed image.

The photographed image at time t0 being the last composite image and the photographed image at time t1 being the latest photographed image after the alignment are then supplied from the alignment unit 32 to the composition unit 33 and composited.

That is, the feature data calculation unit 51 of the composition unit 33 calculates in-focus feature data representing the degree to which a pixel is in focus in each of the photographed image at time t1 being the latest photographed image and the photographed image at time t0 being the last composite image, and supplies a feature data image having the calculated in-focus feature data as a pixel value to the peak calculation unit 52.

The in-focus feature data can be feature data having a large value for an in-focus pixel and a small value for a blurred pixel, for example. Laplacian can be adopted as such in-focus feature data, for example.

The peak calculation unit 52 refers to the feature data image from the feature data calculation unit 51 and calculates (detects) a peak of the in-focus feature data in the pixel at the identical position in each of the photographed image at time t1 being the latest photographed image and the photographed image at time t0 being the last composite image.

FIG. 4 illustrates a pixel p1 corresponding to the object obj1 in the photographed image at time t1 being the latest photographed image and a pixel p0 corresponding to the object obj1 in the photographed image at time t0 being the last composite image and located in the position identical to the pixel p1, where the in-focus feature data of the pixel p0 corresponding to the object obj1 that is in focus is larger than the feature data of the pixel p1 corresponding to the object obj1 that is out of focus. As a result, the in-focus feature data of the pixel p0 is detected as the peak of the in-focus feature data of the pixels p0 and p1 at the identical position, and the detected peak being a result of the detection is supplied from the peak calculation unit 52 to the image composition unit 53.

The image composition unit 53 generates the latest composite image by compositing the photographed image at time t1 being the latest photographed image and the photographed image at time t0 being lire last composite image according to the detected peak from the peak calculation unit 52.

Specifically, the image composition unit 53 generates the latest composite image by selecting, as a pixel of the latest composite image, a pixel with the larger in-focus feature data being the detected peak, namely u pixel corresponding to the object that is more in-focus, between the pixels at the identical position in each of the photographed image at time t1 being the latest photographed image and the photographed image at time t0 being the last composite image.

The composition unit 33 as described above composites the latest photographed image and the last composite image that are aligned by the motion detection in the alignment unit 32. The latest deep-focus composite image can thus be generated by following motion even when an object with some degree of motion is in the latest photographed image and the last composite image.

Figure 5:
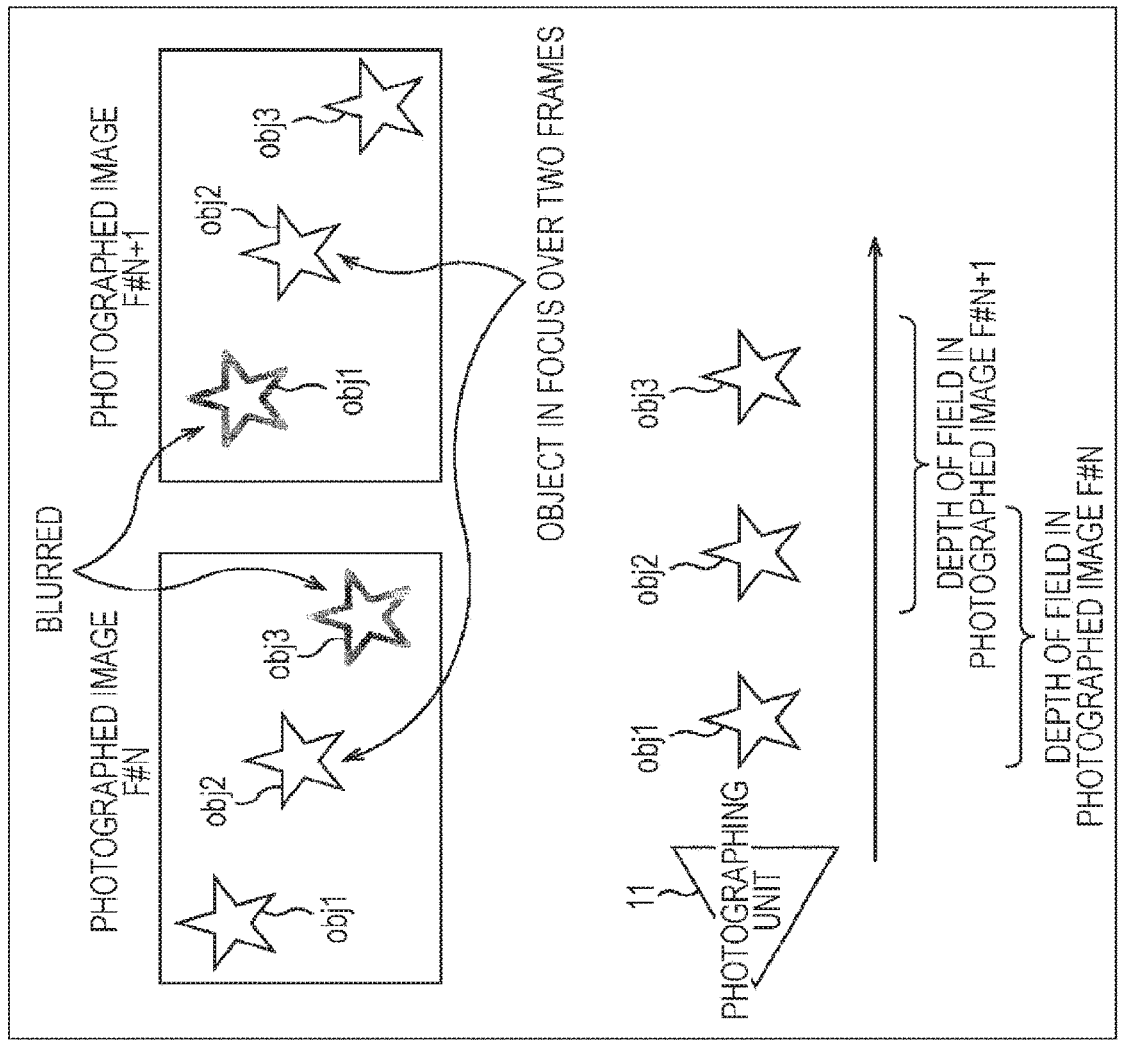
FIG. 5 is a diagram illustrating a photographed image that is photographed while changing a focus position in the photographing unit 11.

FIG. 5 is a diagram illustrating a photographed image that is obtained while changing a focus position in the photographing unit 11.

FIG. 5 illustrates a case where objects obj1, obj2, and obj3 arranged in a real space are photographed while changing the focus position.

Note that the objects obj1, obj2, and obj3 are arranged in this order away from the side of the photographing unit 11.

The focus position is shifted from a front side to a back side (as seen from the side of the photographing unit 11) in photographing the objects obj1 to obj3.

Photographed images F #N and F #N+1 in FIG. 5 are adjacent frames of photographed images, where the photographed image F #N+1 is obtained after the photographed image F #N.

The depth of field when the photographed image F #N is obtained covers the forefront object obj1 and the second forefront object obj2 but does not cover the object obj3 arranged farthest back. Therefore, the objects obj1 and obj2 are in focus while the object obj3 is out of focus in the photographed image F #N.

On the other hand, the depth of field when the photographed image F #N+1 is obtained covers the second forefront object obj2 and the object obj3 arranged farthest back but does not cover the forefront object obj1. Therefore, the objects obj2 and obj3 are in focus while the object obj1 is out of focus in the photographed image F #N+1.

The object obj1 is thus in focus in both of the photographed images F #N and F #N+1.

The focus position is shifted such that, as described above, one or more objects (the object obj2 in FIG. 5) is/are in focus in the adjacent frames of the photographed images F #N and F #N+1, namely, the depths of field of the adjacent frames of the photographed images F #N and F #N+1 overlap in part.

First Operational Example of Medical Observation System

Figure 6:
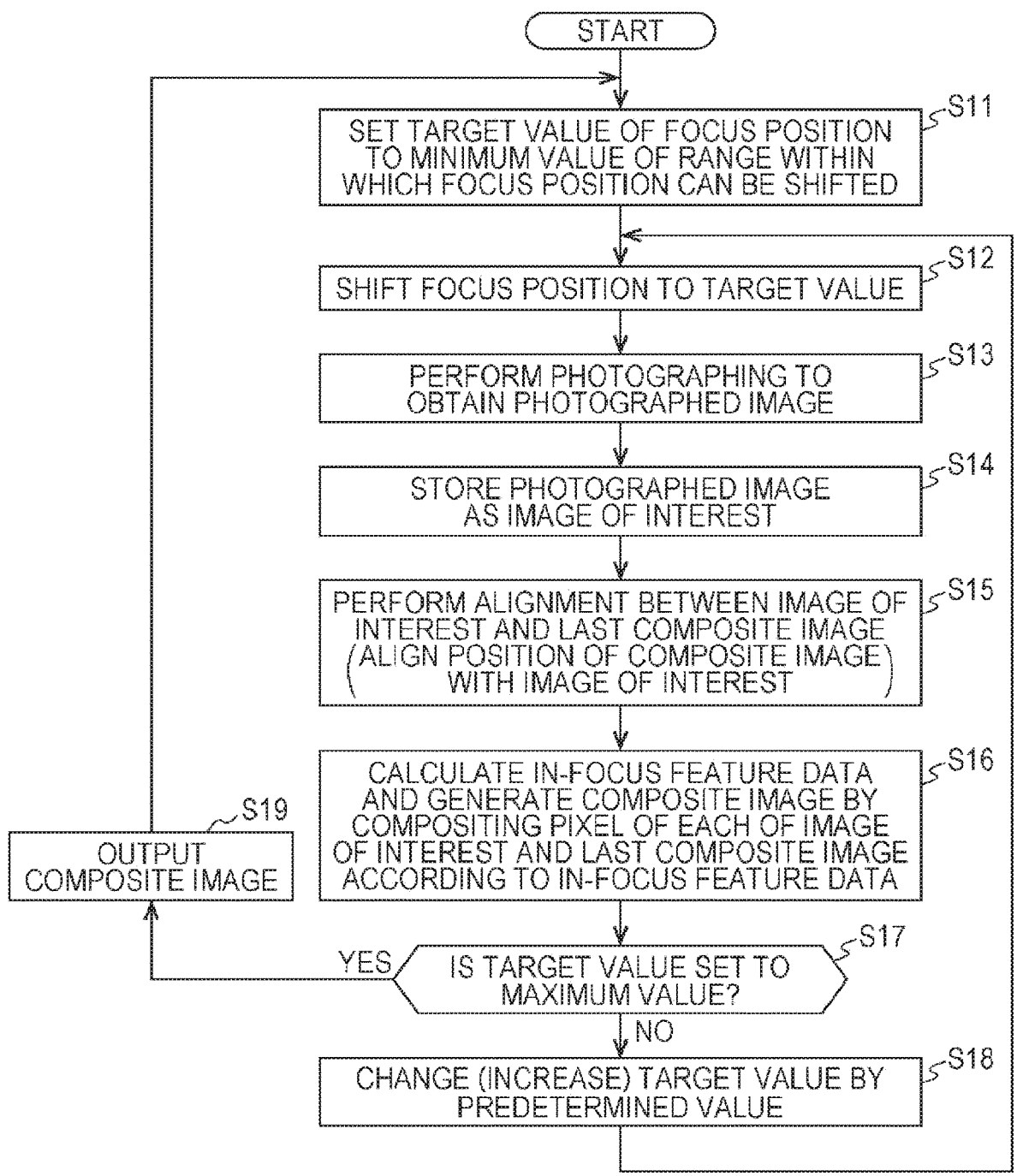
FIG. 6 is a flowchart illustrating a first operational example of the medical observation system.

FIG. 6 is a flowchart illustrating a first operational example of the medical observation system illustrated in FIG. 1.

Specifically, FIG. 6 illustrates an operational example of the medical observation system when the signal processing device 12 is configured as illustrated in FIG. 2.

In step S11, the control unit 35 sets a target value of the focus position to a default value such as a minimum value of a range within which the focus position can be shifted, then the operation proceeds to processing in step S12.

In step S12, the control unit 35 controls the drive control unit 34 to shift the focus position to the target value, then the operation proceeds to processing in step S13.

In step S13, the photographing unit 11 performs photographing to obtain a photographed image while the focus position is at the target value and supplies the photographed image to the frame buffer 31, then the operation proceeds to processing in step S14.

In step S14, the frame buffer 31 stores the photographed image from the photographing unit 11 as an image of interest, then the operation proceeds to processing in step S15.

In step S15, the alignment unit 32 performs alignment between the image of interest being the latest photographed image stored in the frame buffer 31 and the last composite image stored in the frame buffer 31 as described with reference to FIG. 4.

Moreover, in step S15, the alignment unit 32 supplies the aligned image of interest and last composite image to the composition unit 33, then the operation proceeds to processing in step S16.

Here, the composite image stored in the frame buffer 31 is reset, namely deleted from the frame buffer 31, at a predetermined timing.

The composite image is reset at the start of photographing, for example.

Therefore, at the start of photographing, the composite image is reset and not stored in the frame buffer 31.

The composite image can also be reset in step S11 where the target value of the focus position is set to the default value, for example. Moreover, the composite image can be reset when a photographed image not suitable for generating a deep focus composite image is obtained such as when large motion is detected from the photographed image, and a composition restriction condition that restricts composition of the photographed image (and resultant generation of a composite image) is satisfied.

The processing in each of steps S15 and S16 is skipped when the composite image is not stored in the frame buffer 31, in which case the image of interest is stored as the composite image into the frame buffer 31.

In step S16, as described above with reference to FIG. 4, the composition unit 33 calculates the in-focus feature data of the pixel in each of the aligned image of interest and last composite image and, according to the calculated in-focus feature data, composites the image of interest and the last composite image to generate the latest composite image.

Specifically, the composition unit 33 generates the latest composite image by selecting, as a pixel of the latest composite image, the pixel that is more in focus between the pixels in the image of interest and the last composite image according to the in-focus feature data.

The composition unit 33 supplies the latest composite image to the frame buffer 31, which stores the latest composite image by overwriting the last composite image therewith, then the operation proceeds from the processing in step S16 to processing in step S17.

Here, the latest composite image stored in the frame buffer 31 as described above is used as a last composite image in step S15 performed in the next round of operation.

In step S17, the control unit 35 determines whether the target value of the focus position is set to a maximum value of the range within which the focus position can be shifted.

The operation proceeds to processing in step S18 when it is determined in step S17 that the target value is not set to the maximum value of the range within which the focus position can be shifted, namely when the target value is smaller than the maximum value of the range within which the focus position can be shifted.

In step S18, the control unit 35 increases the target value of the focus position by a predetermined value from the current value, then the operation returns to the processing in step S12.

In step S12, as described above, the control unit 35 controls the drive control unit 34 to shift the focus position to the target value. The similar processing is repeated from then on so that the photographed image is obtained while changing the focus position and that the latest photographed image and the last composite image are composited.

On the other hand, the operation proceeds to processing in step S19 when it is determined in step S17 that the target value is set to the maximum value of the range within which die focus position can be shifted, namely when a plurality of photographed images is obtained while shifting the focus position across the range within which the focus position can be shifted.

In step S19, the composition unit 33 outputs the latest composite image to be displayed in the display device 13 (FIG. 1), then the operation returns to the processing in step S11.

In the first operational example, the plurality of photographed images is obtained while shifting the focus position across the range within which the focus position can be shifted, and then the composite image is generated by using all of the plurality of photographed images and output/displayed to/in the display device 13.

Therefore, in the first operational example, the frame rate of the composite image displayed in the display device 13 is lower than the frame rate of the photographed image obtained in the photographing unit 11 by the amount corresponding to the number of frames of the photographed images used to generate the composite image.

Second Operational Example of Medical Observation System

Figure 7:
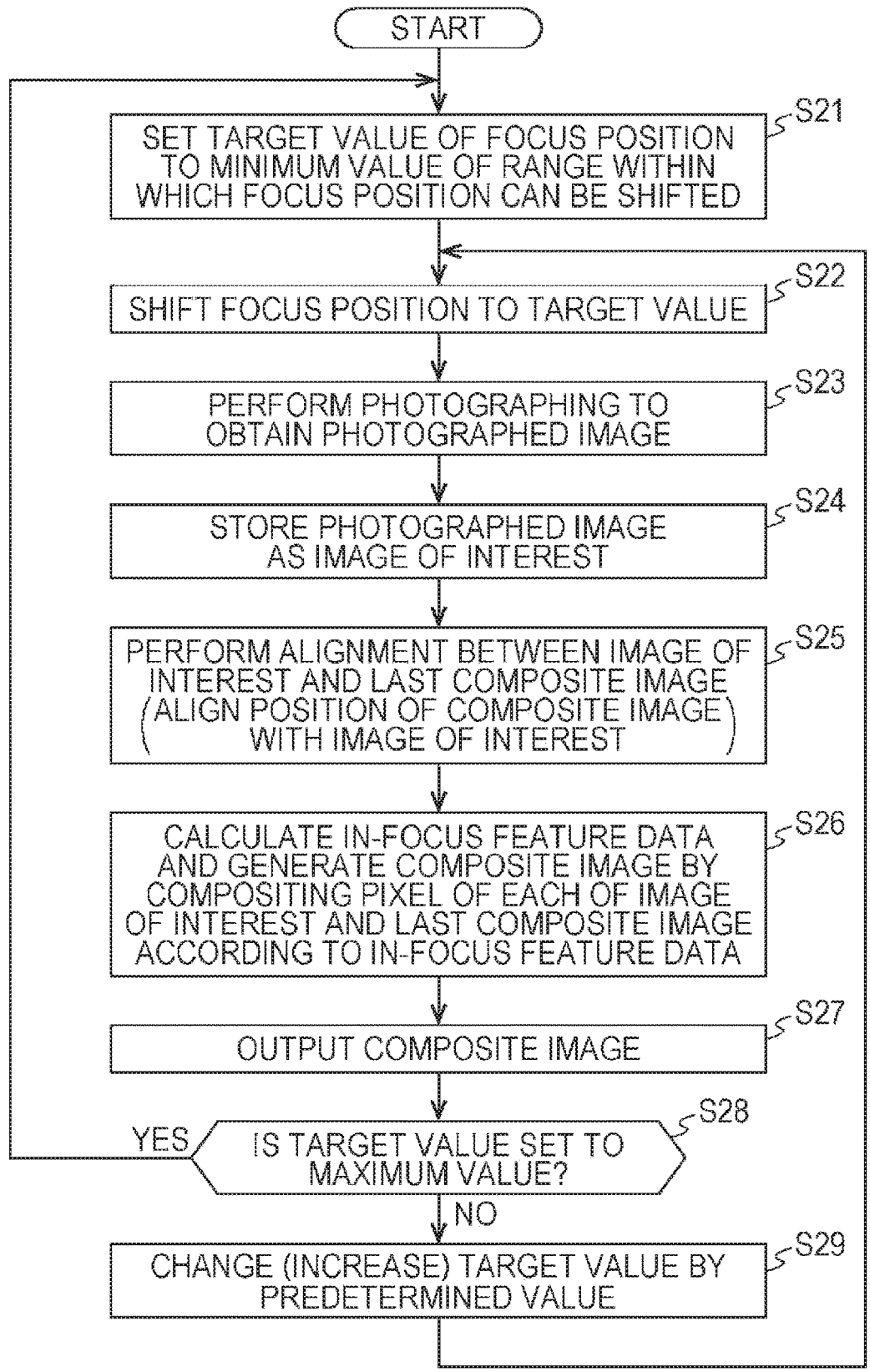
FIG. 7 is a flowchart illustrating a second operational example of the medical observation system.

FIG. 7 is a flowchart illustrating a second operational example of the medical observation system illustrated in FIG. 1.

Specifically, FIG. 7 illustrates another operational example of the medical observation system when the signal processing device 12 is configured as illustrated in FIG. 2.

In the second operational example, processing similar to the processing performed in each of steps S11 to S16 of the first operational example in FIG. 6 is performed in each of steps S21 to S26.

In step S26, the composition unit 33 generates a latest composite image and supplies it to the frame buffer 31, which stoics the latest composite image by overwriting the last composite image therewith, then the operation proceeds to processing in step S27.

In step S27, the composition unit 33 outputs the latest composite image to be displayed in the display device 13 (FIG. 1) as with step S19 of the first operational example in FIG. 6, then the operation proceeds to processing in step S28.

In each of steps S28 and S29, processing similar to the processing performed in each of steps S17 and S18 of the first operational example in FIG. 6 is performed.

In the first operational example of FIG. 6, as described above, the plurality of photographed images is obtained while shifting the focus position across the range within which the focus position can be shifted, and then the composite image is generated by using all of the plurality of photographed images and output/displayed to/in the display device 13.

On the other hand, what is common to the first operational example in the second operational example of FIG. 7 is that a plurality of photographed images is obtained while shifting the focus position across the range within which the focus position can be shifted.

However, in the second operational example, a latest composite image is output/displayed to/in the display device 13 in step S27 every time the latest composite image is generated by using the latest photographed image (image of interest) in step S26 corresponding to S16 of the first operational example.

Therefore, in the second operational example, the frame rate of the composite image displayed in the display device 13 corresponds with the frame rate of the photographed image obtained by the photographing unit 11.

Note that a user can perform an operation or the like to select whether to generate the composite image by using all of the plurality of photographed images obtained while shifting the focus position across the range within which it can be shifted and output the composite image to the display device 13 as described in the first operational example of FIG. 6, or to output the latest composite image to the display device 13 every time the latest composite image is generated by using the latest photographed image as described in the second operational example of FIG. 7.

Between the first and second operational examples, there will be described an example where, as described in the first operational example, the composite image is generated by using all of the plurality of photographed images obtained while shifting the focus position across the range within which the focus position can be shifted and then output to the display device 13.

Third Operational Example of Medical Observation System

Figure 8:
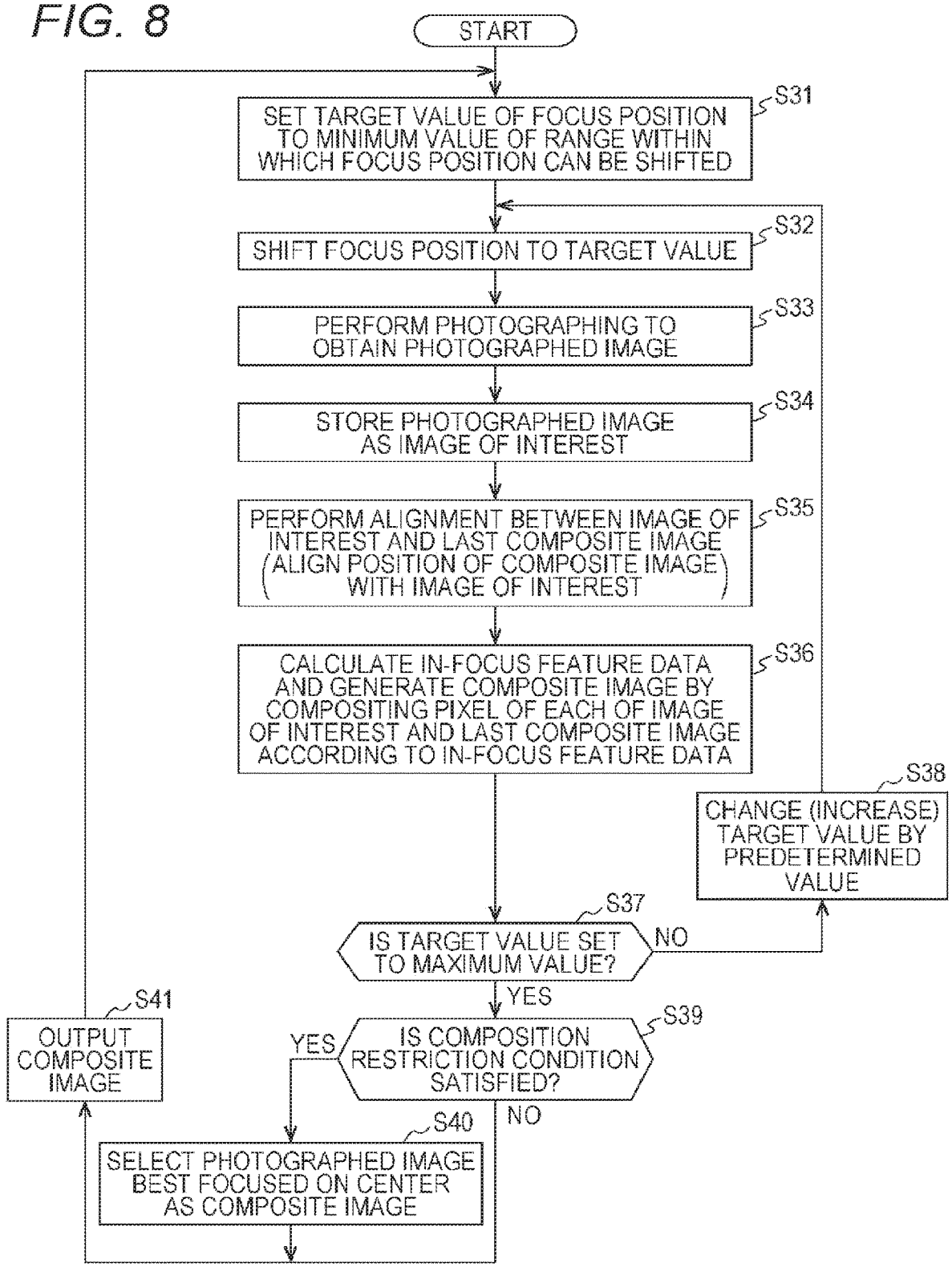
FIG. 8 is a flow-chart illustrating a third operational example of the medical observation system.

FIG. 8 is a flowchart illustrating a third operational example of the medical observation system illustrated in FIG. 1.

Specifically, FIG. 8 illustrates yet another operational example of the medical observation system when the signal processing device 12 is configured as illustrated in FIG. 2.

In the third operational example, processing similar to the processing performed in each of steps S11 to S18 of the first operational example in FIG. 6 is performed in each of steps S31 to S38.

In step S37, as with the corresponding step S17 of the first operational example, the control unit 35 determines whether the target value of the focus position is set to a maximum value of the range within which the focus position can be shifted.

The operation proceeds to processing in step S39 when it is determined in step S37 that the target value is set to the maximum value of the range within which the focus position can be shifted.

In step S39, the control unit 35 determines whether a composition restriction condition that restricts composition of the photographed image (and resultant generation of a composite image) is satisfied.

Here, the composition restriction condition can be a case where a photographed image not suitable for generating a deep focus composite image is obtained or a case where a user does not desire to obtain a deep focus image, for example.

The photographed image not suitable for generating the deep focus composite image is obtained when, for example, reliability of the angle of view adjustment performed on the image of interest and the last composite image is less than or equal to a threshold, the angle of view adjustment being performed in the alignment between the image of interest and the last composite image in step S35.

In the angle of view adjustment, as described with reference to FIG. 4, there is obtained the angle of view with the highest correlation value between the image of interest (photographed image at time t1 being the latest photographed image) and the last composite image (photographed image at time t0 being the last composite image), and the angle of view of the last composite image is adjusted to the angle of view obtained.

The reliability of the angle of view adjustment can be indicated by the correlation value between the image of interest and the last composite image when the angle of view of the last composite image is adjusted, for example.

Moreover, the photographed image not suitable for generating the deep focus composite image is obtained when, for example, reliability of the motion detection performed on the image of interest and the last composite image is less than or equal to a threshold, the motion detection being performed in compositing the image of interest and the last composite image in step S36.

The reliability of the motion detection can be indicated by a value inversely proportional to a Sum of Absolute Difference (SAD) or the like being an evaluation value that is used to detect a motion vector in block matching performed as motion detection and evaluates similarity between blocks, for example.

Furthermore, the photographed image not suitable for generating the deep focus composite image is obtained when, for example, the degree of the motion detected in the image of interest and the last composite image in the motion detection is higher than or equal to a threshold, the motion detection being performed in compositing the image of interest and the last composite image in step S36.

When a user systematically performs panning or zooming by operating the photographing unit 11 or when the degree of motion of an object is large relative to shift speed of the focus position, for example, it is more difficult to align the objects in the image of interest and the last composite image, thereby possibly causing considerable motion blur in a composite image.

The case where the degree of motion detected in the image of interest and the last composite image in the motion detection is higher than or equal to the threshold can be set as the composition restriction condition to be able to prevent generation of the aforementioned composite image with considerable motion blur.

The user does not desire to obtain the deep focus image when, for example, a photographed image includes a living body such as a surgical site of a human body undergoing an operation as well as a treatment tool such as forceps used to perform a treatment on the surgical site where the treatment tool is intentionally moved (the treatment tool is moved toward the surgical site, for example) by the user (who operates the treatment tool).

One can see whether the treatment tool is in motion by image recognition recognizing that the treatment tool is included in the photographed image and detecting motion of the treatment tool, for example.

One can also see whether the treatment tool is in motion on the basis of a suite of a button (not shown) operated to be in an on state when the treatment tool is handled by the user, for example.

Moreover, the user does not desire to obtain the deep focus image when, for example, a button (not shown) operated when the user does not desire to obtain the deep focus image is operated.

The operation proceeds to processing in step S40 when it is determined in step S39 that the composition restriction condition is satisfied.

In step S40, the composition unit 33 reads from the frame buffer 31 one of the plurality of photographed images used to generate the latest composite image, namely a single frame of photographed image focused on the center or the like through the alignment unit 32.

The composition unit 33 then selects the photographed image read from the frame buffer 31 and focused on the center as the latest composite image, then the operation proceeds from the processing in step S40 to processing in step S41.

On the other hand, the operation skips the processing in step S40 and proceeds to the processing in step S41 when it is determined in step S39 that the composition restriction condition is not satisfied.

In step S41, the composition unit 33 outputs the latest composite image to be displayed in the display device 13 (FIG. 1) as with step S19 of the first operational example in FIG. 6, then the operation returns to the processing in step S31.

In the third operational example of FIG. 8, the composite image formed by compositing the plurality of photographed images obtained while changing the focus position is output/displayed to/in the display device 13 when the composition restriction condition is not satisfied whereas, when the composition restriction condition is satisfied, one of the plurality of photographed images is output/displayed to/in the display device 13 due to output restriction on the composite image formed by compositing the plurality of photographed images obtained while changing the focus position.

As a result, there can be prevented a case where the composite image formed by compositing the plurality of photographed images obtained while changing the focus position is displayed in the display device 13 when the user intentionally moves the treatment tool largely toward the surgical site and does not particularly feel the need of EDoF, for example.

Moreover, there can be prevented a case where an image with considerable motion blur is displayed in the display device 13 when the plurality of photographed images with a large degree of motion caused by strong shaking of the photographing unit 11 is obtained and composited, for example.

On the other hand, it is desirable for the medical observation system being medical equipment to prevent interruption of the image displayed in the display device 13 as much as possible and keep displaying the image in the display device 13 considering the nature of the system.

In the third operational example of FIG. 8, the photographed image focused on the center instead of the composite image with considerable motion blur is displayed in the display device 13 when the composition restriction condition is satisfied, namely when the composite image with the considerable motion blur caused by strong shaking of the photographing unit 11 is generated, for example.

As a result, there can be prevented displaying of the composite image with considerable motion blur in the display device 13 as well as interruption of the image displayed in the display device 13.

Second Configuration Example of Signal Processing Device 12

Figure 9:
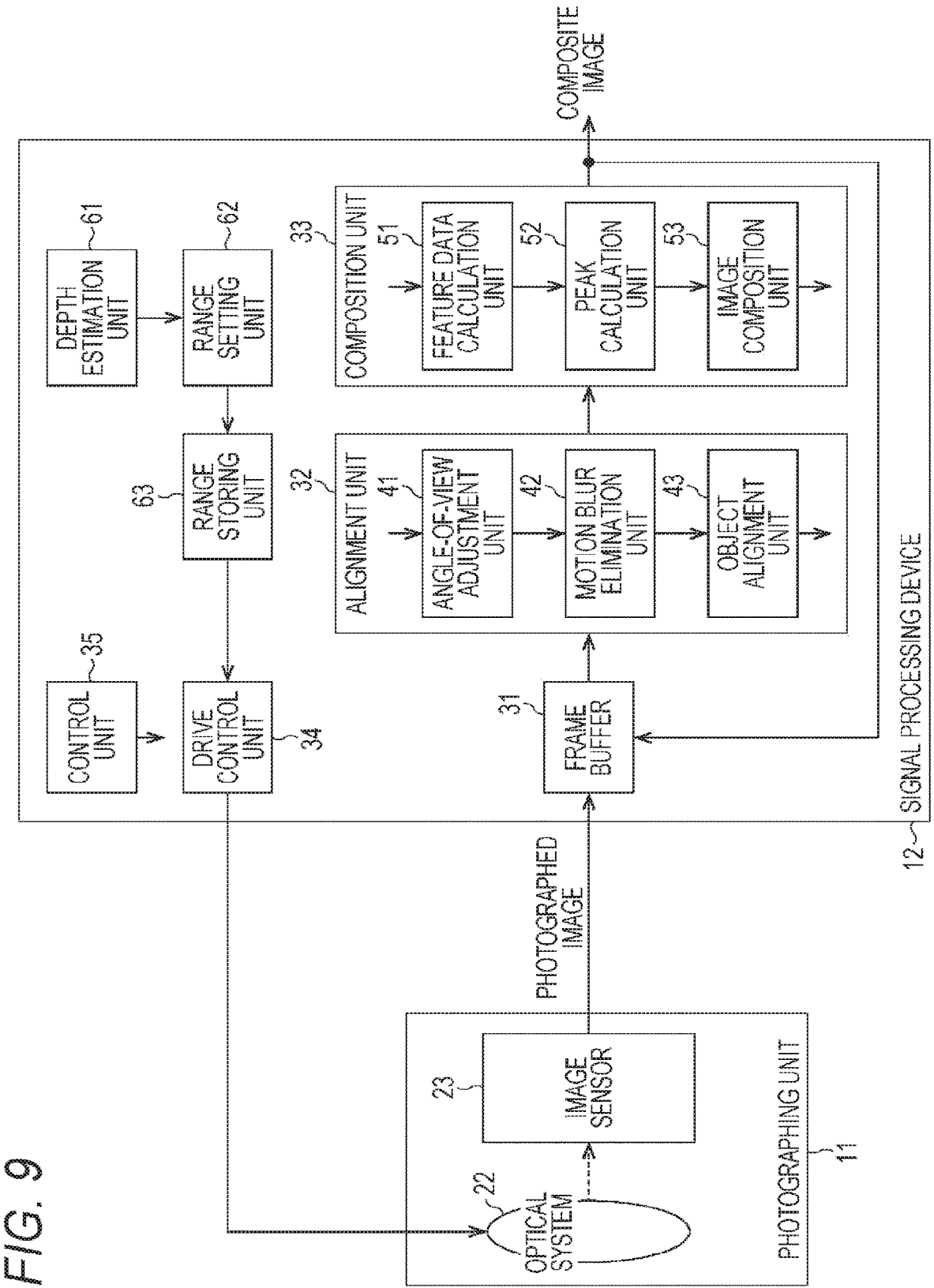
FIG. 9 is a block diagram illustrating a second configuration example of the signal processing device 12.

FIG. 9 is a block diagram illustrating a second configuration example of the signal processing device 12 in FIG. 1.

Note that in the figure, a pan corresponding to the one in FIG. 2 is assigned the same reference numeral as that in FIG. 2 to omit description of such part as appropriate.

The signal processing device 12 in FIG. 9 includes a frame buffer 31 to a control unit 35 as well as a depth estimation unit 61, a range setting unit 62 and a range storing unit 63.

Therefore, what is common to FIG. 2 in FIG. 9 is that the signal processing device 12 includes the frame buffer 31 to the control unit 35.

The signal processing device 12 in FIG. 9 is however different from that in FIG. 2 in that the depth estimation unit 61, the range setting unit 62 and the range storing unit 63 are newly provided.

The depth estimation unit 61 estimates the depth of an object in a photographed image obtained by a photographing unit 11 and supplies a depth map in which depth information indicating the depth is registered to the range setting unit 62.

Here, for example, the depth of the object can be estimated from a parallax between an L image and an R image forming a 3D image photographed by the photographing unit 11 when the photographing unit 11 is a so-called 3D camera capable of photographing a 3D image.

The depth can also be estimated by measuring Time of Flight (ToF) with use of a laser or irradiating the object with a specific pattern such as textured light, for example. Moreover, the depth of the object can be estimated on the basis of a state of an optical system 22 controlled by an Auto Focus (AF) function when the medical observation system of FIG. 1 is equipped with the AF function.

The range setting unit 62 uses the depth map from the depth estimation unit 61 as appropriate, sets a range within which the locus position is shifted (hereinafter also referred to as a focus shift range) according to an operation of a user or the like, and supplies the range to the range storing unit 63.

The range storing unit 63 stores the focus shift range supplied from the range setting unit 62.

While the drive control unit 34 of the signal processing device 12 in FIG. 2 shifts the focus position across the range within which the focus position can be shifted (from the minimum value to the maximum value of the range within which the focus position can be shifted), a drive control unit 34 of the signal processing device 12 in FIG. 9 shifts the focus position across the focus shift range stored in the range storing unit 63.

Accordingly, the photographing unit 11 of FIG. 9 performs photographing to obtain a photographed image while changing the focus position within the focus shift range set according to the user operation.

Figure 10:
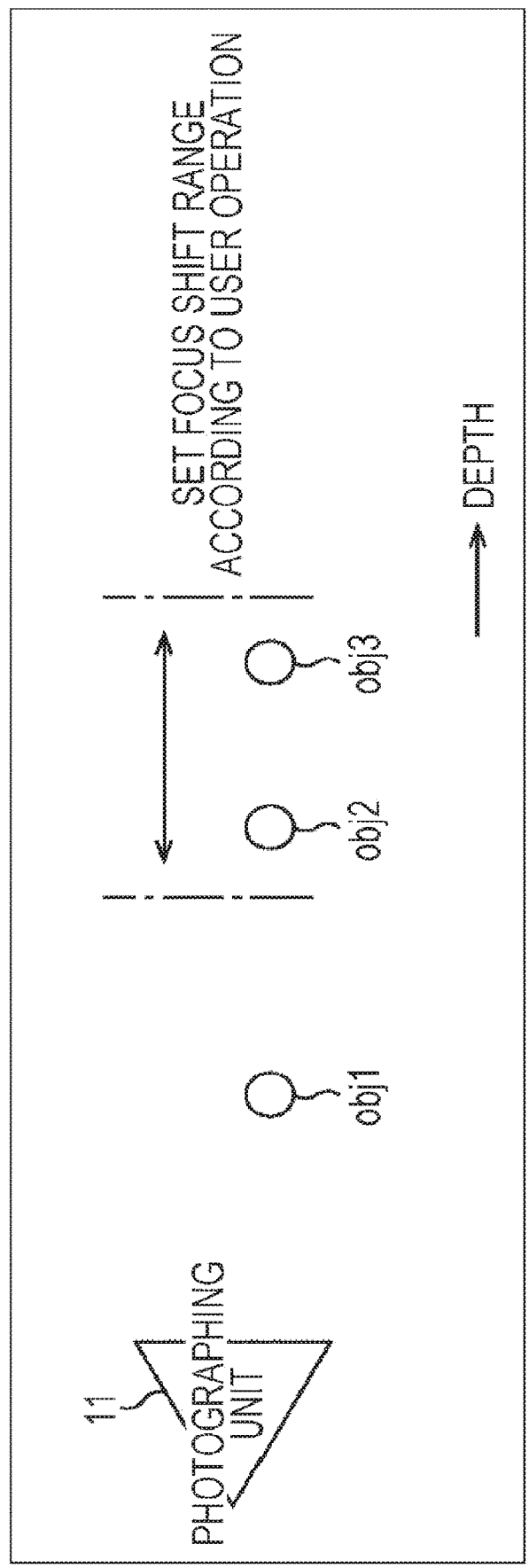
FIG. 10 is a diagram illustrating an example of setting a focus shift range in a range setting unit 62.

FIG. 10 is a diagram illustrating an example of setting the focus shift range in the range setting unit 62.

As with FIG. 5, objects obj1, obj2, and obj3 in FIG. 10 are arranged in this order toward the back in a real space.

Then, as illustrated in FIG. 10, the focus shift range is set such that positions of the two objects obj2 and obj3 at the back among the objects obj1 to obj3 are included as the focus positions.

Assuming that the positions of the objects obj1 to obj3 are included in the range within which the focus position can be shifted and when the focus shift range is set to the range within which the focus position can be shifted, an image in which all the objects obj1 to obj3 are in focus is generated as a composite image.

On the other hand, when the focus shift range is set to include the positions of the two objects obj2 and obj3 among the objects obj1 to obj3 as illustrated in FIG. 10, an image in which the two objects obj2 and obj3 out of the objects obj1 to obj3 are in focus is generated as a composite image.

As a result, the locus position in obtaining the photographed image used to generate the composite image can be limited by setting the focus shift range according to the user operation as described above. The limitation on the focus position can reduce the number of frames of the photographed images used to generate the composite image and, as a result, a composite image to be displayed in a display device 13 can be generated at a shorter interval to be able to increase the frame rate of the composite image to a high frame rate.

Fourth Operational Example of Medical Observation System

Figure 11:
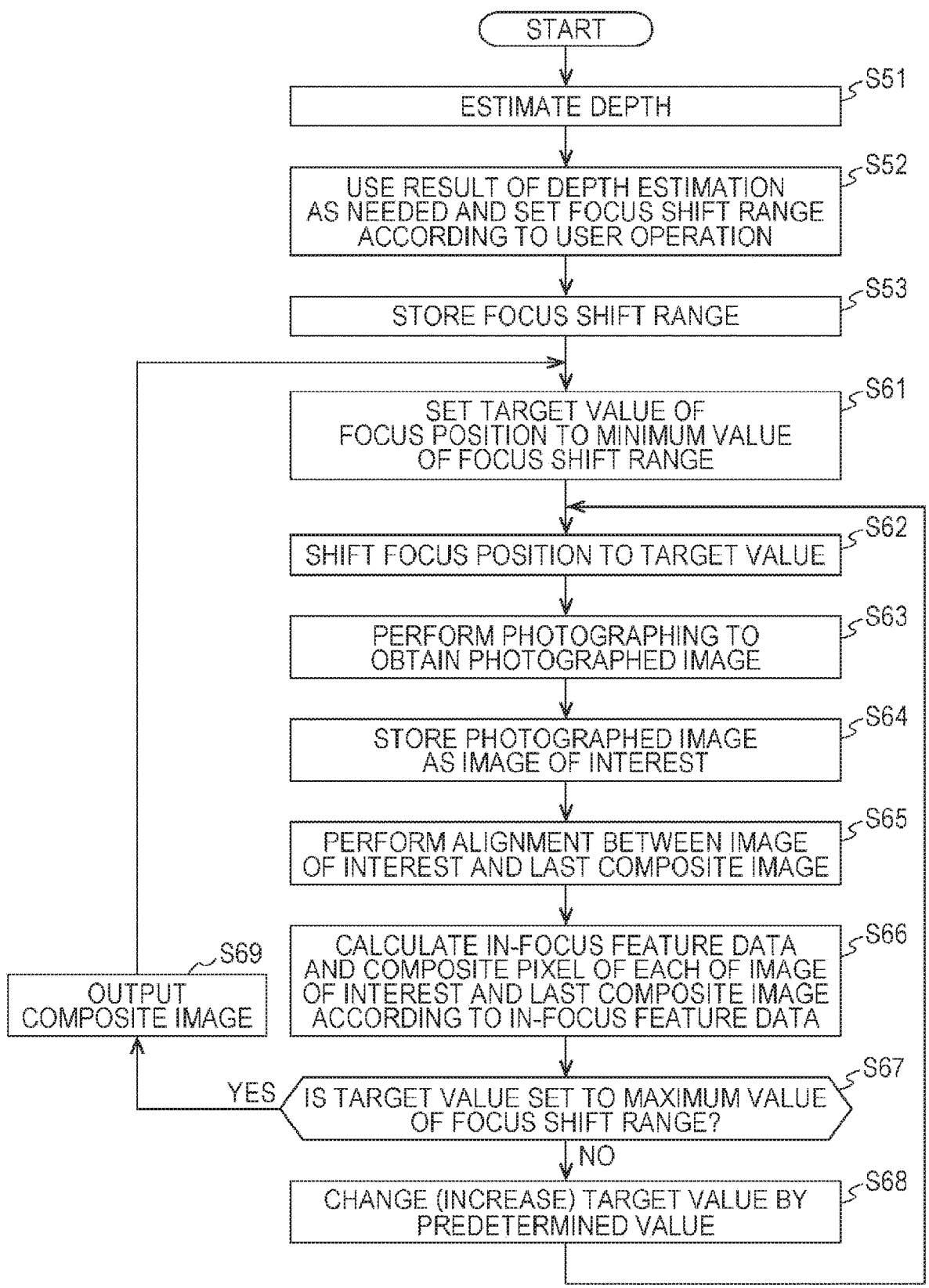
FIG. 11 is a flowchart illustrating a fourth operational example of the medical observation system.

FIG. 11 is a flowchart illustrating a fourth operational example of the medical observation system illustrated in FIG. 1.

Specifically, FIG. 11 illustrates an operational example of the medical observation system when the signal processing device 12 is configured as illustrated in FIG. 9.

In the fourth operational example, the depth estimation unit 61 in step S51 estimates the depth, generates a depth map in which depth information of an object is registered and supplies the depth map to the range setting unit 62, then the operation proceeds to processing in step S52.

In step S52, the range setting unit 62 waits for a user operation or the like and, according to the operation, sets a focus shift range within which the focus position is shifted and supplies it to the range storing unit 63, then the operation proceeds to processing in step S53.

Here, the user can specify the focus shift range by operating a touch panel that is not shown or the like.

The user can specify the focus shift range by inputting an absolute distance in millimeters (mm) as the minimum value and maximum value of the focus shift range, for example.

The user can also specify the focus shift range by inputting the range toward the front and back in the depth direction from the center being the focus position (in-focus position) determined by AF, for example.

The user can also specify the focus shift range by specifying the object in the photographed image obtained by the photographing unit 11, for example.

In this case, the range setting unit 62 uses the depth map obtained in the depth estimation unit 61 and sets the focus shift range.

That is, when the user specifies the object in an image displayed in the display device 13, for example, the range setting unit 62 refers to the depth map and acknowledges a range in the depth direction where the object specified by the user is present. The range setting unit 62 then sets the range in the depth direction where the object specified by the user is present as the locus shift range.

When the user specifies a plurality of objects, the range setting unit 62 sets, as the focus shift range, a range between positions corresponding to the forefront object and the object located farthest back among the plurality of objects.

Note that the focus shift range is set within the range the focus position can be shifted.

The signal processing device 12 of FIG. 9 can also be configured without including the depth estimation unit 61 when the range setting unit 62 does not use the depth map in setting the focus shift range.

In step S53, the range storing unit 63 stores the focus shift range supplied from the range setting unit 62.

Here, the focus shift range stored in the range storing unit 63 is updated every time the user performs an operation to specify the focus shift range.

Following step S53, the operation proceeds to processing in step S61, from which on the focus position is shifted across the focus shift range stored in the range storing unit 63 to obtain a photographed image and generate a composite image.

Specifically, a control unit 35 in step S61 sets a target value of the focus position to a default value such as the minimum value of the focus shift range stored in the range storing unit 63, then the operation proceeds to processing in step S62.

In each of steps S62 to S66, processing similar to the processing performed in each of steps S12 to S16 of the first operational example in FIG. 6 is performed.

The operation then proceeds from the processing in step S66 to processing in step S67, in which the control unit 35 determines whether the target value of the focus position is set to the maximum value of the focus shift range stored in the range storing unit 63.

The operation proceeds to processing in step S68 when it is determined in step S67 that the target value is not set to the maximum value of the focus shift range, namely when the target value is smaller than the maximum value of the focus shift range.

As with step S18 of the first operational example in FIG. 6, the control unit 35 in step S68 increases the target value of the focus position by a predetermined value from the current value, then the operation returns to the processing in step S62, from which on the similar processing is repeated.

Accordingly, the photographed image is obtained while changing the focus position across the focus shift range set according to the user operation, and then the composite image is generated.

On the other hand, the operation proceeds to processing in step S69 when it is determined in step S67 that the target value is set to the maximum value of the focus shift range, namely when a plurality of photographed images is obtained while shifting the focus position across the focus shift range.

In step S69, a composition unit 33 outputs a latest composite image to be displayed in the display device 13 (FIG. 1) as with step S19 of the first operational example in FIG. 6, then the operation returns to the processing in step S61.

In the fourth operational example, as described above, the plurality of photographed images is obtained while shifting the focus position across the focus shift range set according to the user operation, and the composite image is generated by using the plurality of photographed images.

As a result, there can be displayed a composite image in which only the object in the depth range intended (desired) by the user is in focus.

Moreover, the time it takes to shift the focus position is reduced when the focus shift range set according to the user operation is narrower than the range within which the focus position can be shifted, whereby the frame rate of the composite image displayed in the display device 13 can be increased to a high frame rate.

Third Configuration Example of Signal Processing Device 12

Figure 12:
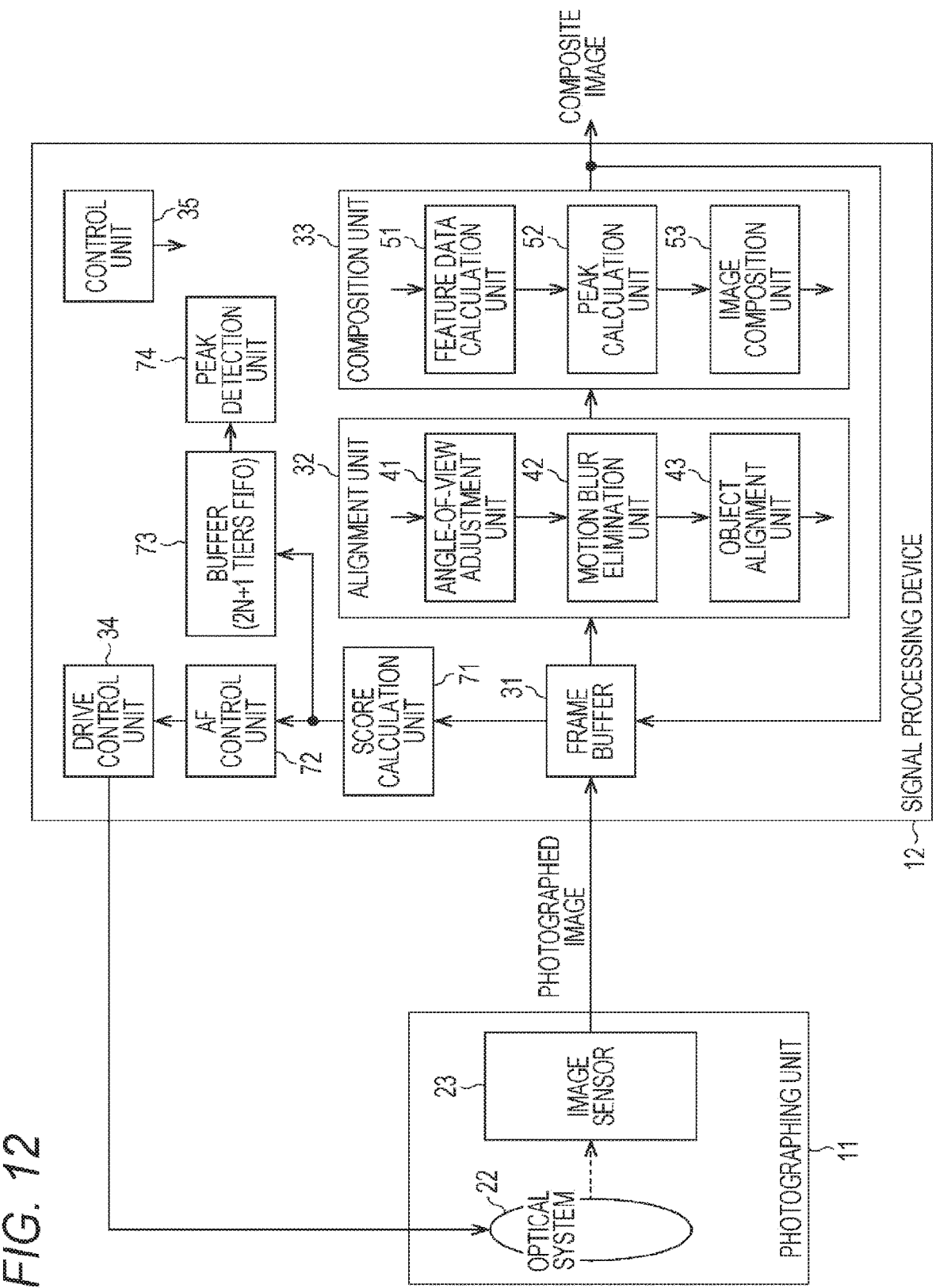
FIG. 12 is a block diagram illustrating a third configuration example of the signal processing device 12.

FIG. 12 is a block diagram illustrating a third configuration example of the signal processing device 12 of FIG. 1.

Note that in the figure, a part corresponding to the one in FIG. 2 is assigned the same reference numeral as that in FIG. 2 to omit description of such part as appropriate.

The signal processing device 12 in FIG. 12 includes a frame buffer 31 to a control unit 35 as well as a score calculation unit 71, an AF control unit 72, a buffer 73 and a peak detection unit 74.

Therefore, what is common to FIG. 2 in FIG. 12 is that the signal processing device 12 includes the frame buffer 31 to the control unit 35.

The signal processing device 12 in FIG. 12 is however different from that in FIG. 2 in that the score calculation unit 71, the AF control unit 72, the buffer 73 and the peak detection unit 74 are newly provided.

The signal processing device 12 in FIG. 12 has an AF function.

Specifically, the score calculation unit 71 calculates a focus score that evaluates focus in a (latest) photographed image stored in the frame buffer 31.

The focus score can be indicated by a physical quantity representing the degree of contrast in the photographed image, for example. A contrast AF method is employed in this case.

The score calculation unit 71 sets an AF frame demarcating the range of the photographed image for which the focus score is calculated at a predetermined position, or at the center of the photographed image, for example. The score calculation unit 71 then uses the photographed image within the AF frame to calculate the focus score and supplies the score to the AF control unit 72 and the buffer 73.

The AF control unit 72 controls the AF according to the focus score supplied from the score calculation unit 71.

Specifically, the AF control unit 72 determines a shift amount (including a direction) of the focus position such that the focus position is shifted to have a higher focus score, and controls the drive control unit 34 such that the focus position is shifted by the shift amount.

The buffer 73 stores the focus score from the score calculation unit 71. The buffer 73 can be formed of a First In First Out (FIFO) memory with 2N+1 tiers, for example, in which case the buffer 73 can store latest 2N+1 frames of focus scores.

The peak detection unit 74 detects a peak, namely a local maximum score being a local maximum value (including the maximum value), from the focus score stored in the buffer 73 and supplies the detected local maximum score to the control unit 35.

Figure 13:
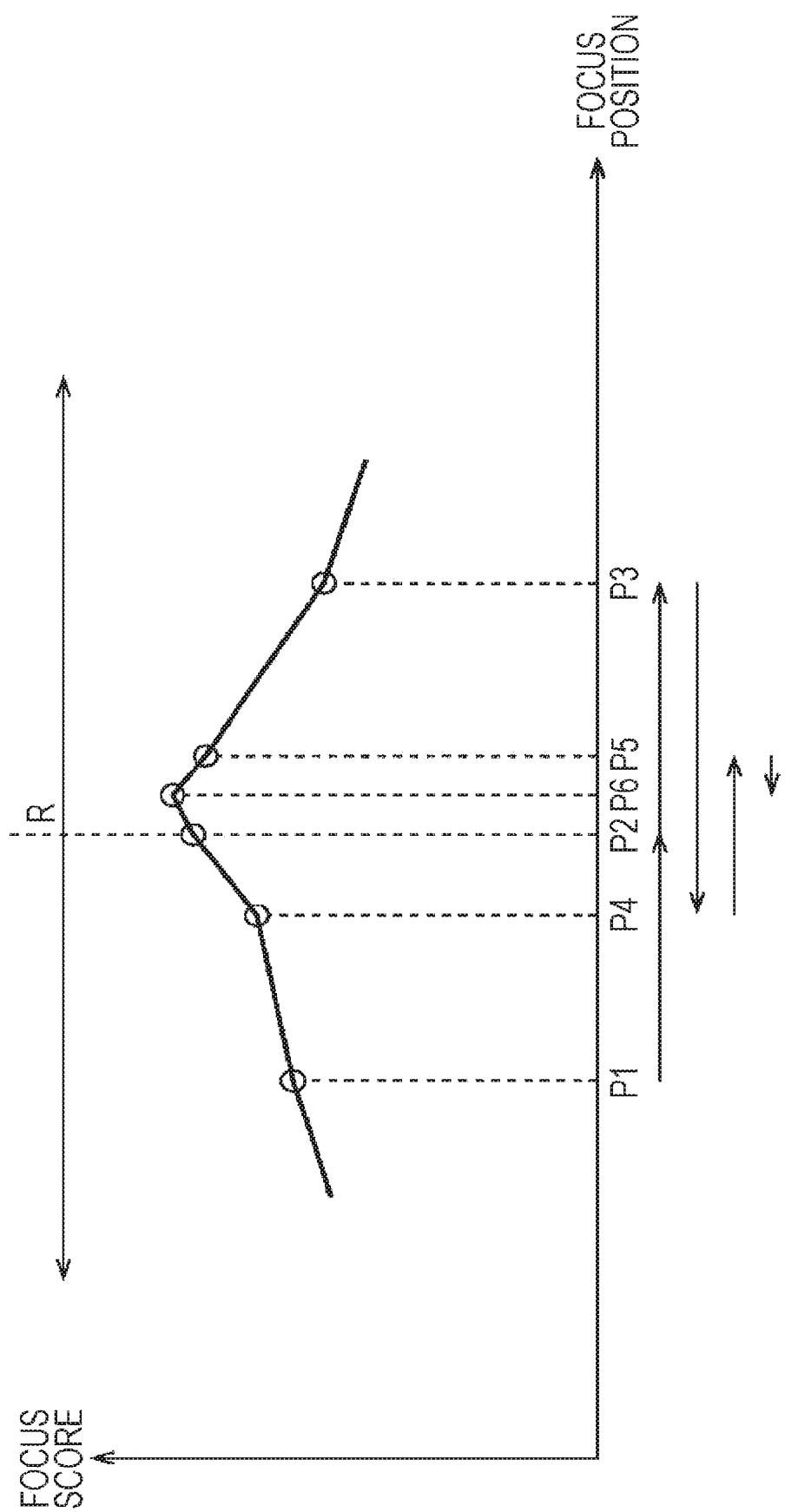
FIG. 13 is a graph illustrating an example of a relationship between a focus position and a focus score.

FIG. 13 is a graph illustrating an example of a relationship between the focus position anti the focus score.

FIG. 13 illustrates an example where the focus position is shifted in the order of positions P1, P2, P3, P4, P5, and P6 by the contrast AF method and shifted to the in-focus position P6 in the end at which the focus score has the maximum value.

That is, in the contrast AF method, the focus position is shifted to have a higher focus score until the focus position is shifted to the vicinity of the in-focus position P6. Once the focus position reaches the vicinity of the in-focus position P6, the focus position is shifted to straddle the in-focus position P6 (to go back and forth over the in-focus position P6) in order to detect the in-focus position P6.

FIG. 13 illustrates the case where the focus position is first shifted to the right in the figure in the order of the positions P1, P2, and P3. The focus score increasing as the focus position is shifted from the position P1 to the position P2 decreases at the position P3, whereby the focus position is shifted to the left in a reverse direction from the position P3 to the position P4. After that, the focus position is again shifted to the right from the position P4 to the position P5, and again to the left from the position P5 to reach the in-focus position P6.

Therefore, in the contrast AF method as described above, it takes time for the focus position to be shifted to the in-focus position P6 since the focus position is shifted to straddle the in focus position P6 in the vicinity thereof.

The signal processing device 12 in FIG. 12 detects the peak of the focus score, namely the local maximum score (not necessarily the maximum value), from the focus score and generates a composite image by using composition target images being a plurality of photographed images obtained at the focus position that is the focus position corresponding to the local maximum score and is in a predetermined range including a peak position.

Here, the focus score increasing from the position P1 to the position P2 decreases at the position P3 in FIG. 13, whereby it is detected that the focus score at the position P2 is the local maximum score and thus the position P2 is the peak position.

Once the local maximum score is detected, the signal processing device 12 in FIG. 12 stops shifting the focus position performed as AF. Moreover, a predetermined range R including the peak position P2 that is the position P2 at which the local maximum score is detected is set as a composition target focus range R being the range of the focus position of the photographed images to be the composition target images.

The composite image is then generated by using the composition target images being the photographed images obtained at the focus position in the composition target focus range R.

Note that the predetermined range R is set within the range in which the focus position can be shifted.

When the composite image is generated as described above in conjunction with the AF function and by using the composition target images being the plurality of photographed images obtained at the focus position in the predetermined range R that includes the peak position of the focus score, a deep locus composite image can be obtained by using the photographed images obtained up until the focus position is shifted to the in-focus position P6 by the AF function.

Therefore, the focus position need only be shifted to the vicinity of the in-focus position P6, not to the in-focus position P6, in AF so that AF can be substantially increased in speed.

Moreover, there can be prevented a case where, in generating a composite image, a photographed image is obtained at a focus position away from the position of the object in a real space photographed by the photographing unit 11. In other words, there can be prevented a case where a photographed image not focused on any object is obtained. The composite image can be generated faster as a result, and thus the frame rate of the composite image can be increased to a high frame rate.

Fifth Operational Example of Medical Observation System

Figure 14:
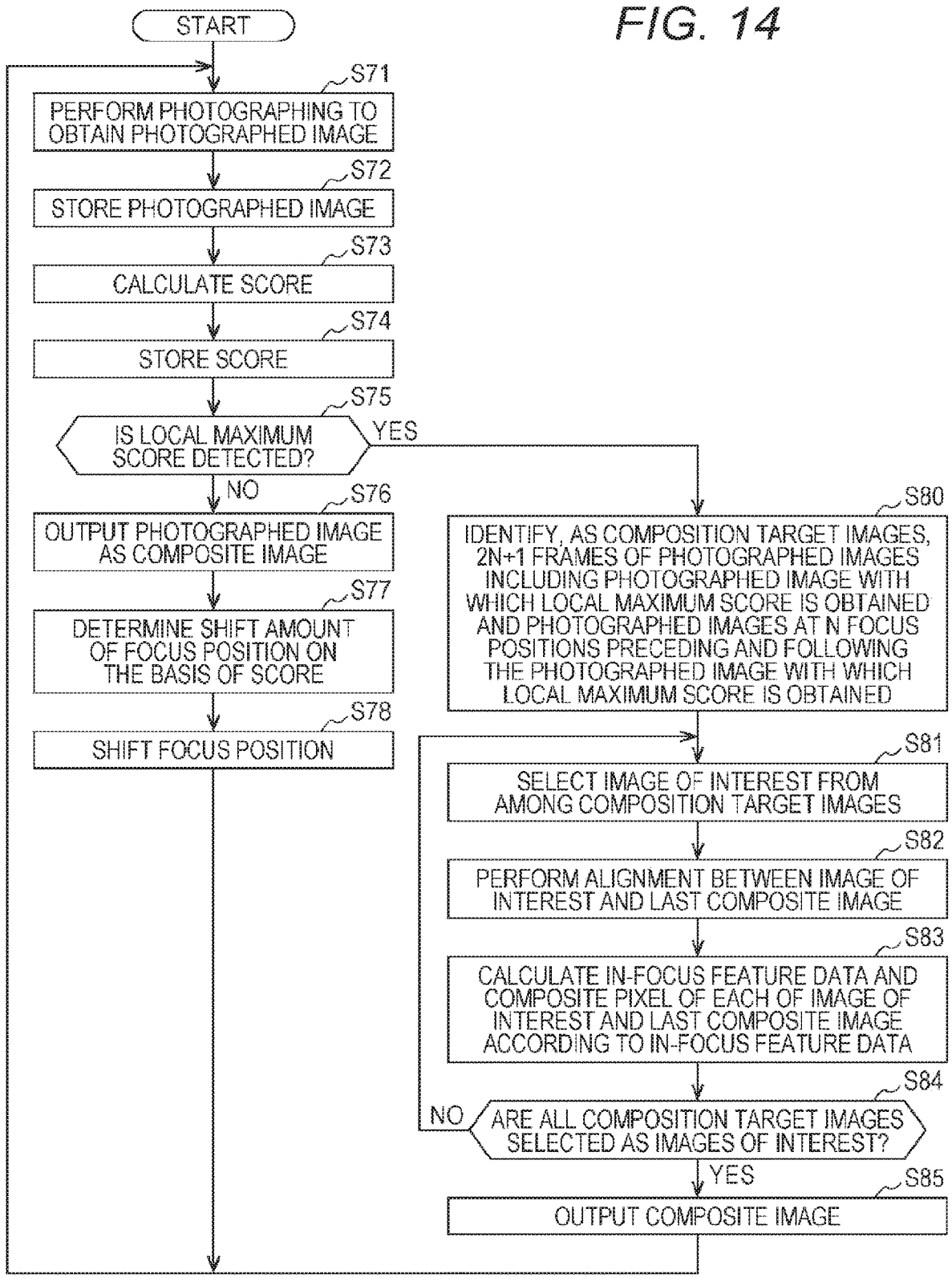
FIG. 14 is a flowchart illustrating a fifth operational example of the medical observation system.

FIG. 14 is a flow chart illustrating a fifth operational example of the medical observation system illustrated in FIG. 1.

Specifically, FIG. 14 illustrates an operational example of the medical observation system when the signal processing device 12 is configured as illustrated in FIG. 12.

In step S71, a photographing unit 11 performs photographing to obtain a photographed image and supplies the photographed image to the frame buffer 31, then the operation proceeds to processing in step S72.

In step S72, the frame buffer 31 stores the photographed image supplied from the photographing unit 11, then the operation proceeds to processing in step S73, In step S73, the score calculation unit 71 calculates a focus score by using a photographed image within the AF frame set at a predetermined position among the (latest) photographed images stored in the frame buffer 31 and supplies the focus score to the AF control unit 72 and the buffer 73, then the operation proceeds to processing in step S74.

In step S74, the buffer 73 stores the focus score supplied from the score calculation unit 71, then the operation proceeds to processing in step S75.

In step S75, the peak detection unit 74 performs detection of a local maximum score from the focus score stored in the buffer 73 and determines whether the local maximum score is successfully detected.

The operation proceeds to processing in step S76 when it is determined in step S75 that the local maximum score is not successfully detected. In step S76, the composition unit 33 reads the latest photographed image from the frame buffer 31 through the alignment unit 32 and outputs the latest photographed image to a display device 13 as a latest composite image, then the operation proceeds to processing in step S77. Step S76 can be skipped here.

In step S77, the AF control unit 72 determines a shift amount of the focus position to have a higher focus score according to the focus score supplied from live score calculation unit 71, then the operation proceeds to processing in step S78.

In step S78, the AF control unit 72 controls the drive control unit 34 to shift the focus position by the shift amount determined in step S77, whereby the focus position is shifted by the shift amount determined in step S77.

The operation thereafter returns from the processing in step S78 to step S71, and the processing in each of steps S71 to S78 is repeated until it is determined in step S75 that the local maximum score is detected.

The operation then proceeds to processing in step S80 when it is determined in step S75 that the local maximum score is detected.

In step S80, the control unit 35 sets a predetermined range R of the focus position with the center being a peak position that is the focus position at which the local maximum score is detected as a composition target focus range R being the range of the focus position of the photographed images to be used as composition target images.

Moreover, from among the photographed images obtained at the focus positions within the composition target focus range R, the control unit 35 identifies 2N+1 frames of photographed images as the composition target images, the 2N+1 frames of photographed images including 2N frames of photographed images obtained at N focus positions preceding and following the peak position and a single frame of photographed image obtained at the focus position being the peak position.

Note that when there is less than N frames of photographed images obtained at the focus positions preceding or following the peak position among the photographed images obtained at the locus positions within the composition target focus range R, all photographed images obtained at the focus positions preceding or following the peak position can be identified us live composition target images among the photographed images obtained at the focus positions within the composition target focus range R, for example.

Alternatively, the photographed images can be obtained while shifting the focus position within the composition target focus range R such that N frames of photographed images are obtained at the focus positions preceding and following the peak position.

The operation proceeds to processing in step S81 after the composition target images are identified as described above in step S80.

Here, in the fifth operational example of FIG. 14, the composite image stored in the frame buffer 31 can be reset when the composition target images are identified in step S80.

In step S81, the alignment unit 32 selects, as an image of interest, one photographed image not yet selected as the image of interest from among the photographed images being the composition target images stored in the frame buffer 31, then the operation proceeds to processing in step S82.

As with step S15 of the first operational example in FIG. 6, the alignment unit 32 in step S82 performs alignment between the image of interest and the last composite image stored in the frame buffer 31 and supplies the aligned image of interest and last composite image to the composition unit 33, then the operation proceeds to processing in step S83.

Here, as is the case with the example in FIG. 6, the processing in each of steps S82 and S83 is skipped when the composite image is not stored in the frame buffer 31, in which case the image of interest is stored as the composite image into the frame buffer 31.

As with step S16 of the first operational example in FIG. 6, the composition unit 33 in step S83 calculates in-focus feature data of a pixel in each of the aligned image of interest and last composite image and, according to the in-focus feature data, composites the image of interest and the last composite image to generate a latest composite image.

The composition unit 33 also supplies the latest composite image to the frame buffer 31, which stores the latest composite image by overwriting the last composite image therewith, then the operation proceeds from the processing in step S83 to processing in step S84.

In step S84, the alignment unit 32 determines whether all the composition target images are selected as the images of interest.

When it is determined in step S84 that not all the composition target images are selected as the images of interest yet, the operation returns to the processing in step S81, from which on the similar processing is repeated.

On the other hand, the operation proceeds to processing in step S85 when it is determined in step S84 that all the composition target images are selected as the images of interest, or when a composite image using all the composition target images is generated as the latest composite image.

In step S85, the composition unit 33 outputs the latest composite image to be displayed in the display device 13, then the operation returns to the processing in step S71.

Note that while the focus position is shifted until the local maximum score, namely the peak position, is detected as the AF function performed in steps S71 to S78 in FIG. 14, the AF function can also be performed to shift the locus position until the maximum value of the focus score is detected, namely until the in-focus position is detected, for example.

In this case, in the AF function, the composite image can be generated by using composition target images including a photographed image obtained at the in-focus position and photographed images obtained at a plurality of focus positions preceding and following the in-focus position.

Fourth Configuration Example of Signal Processing Device 12

Figure 15:
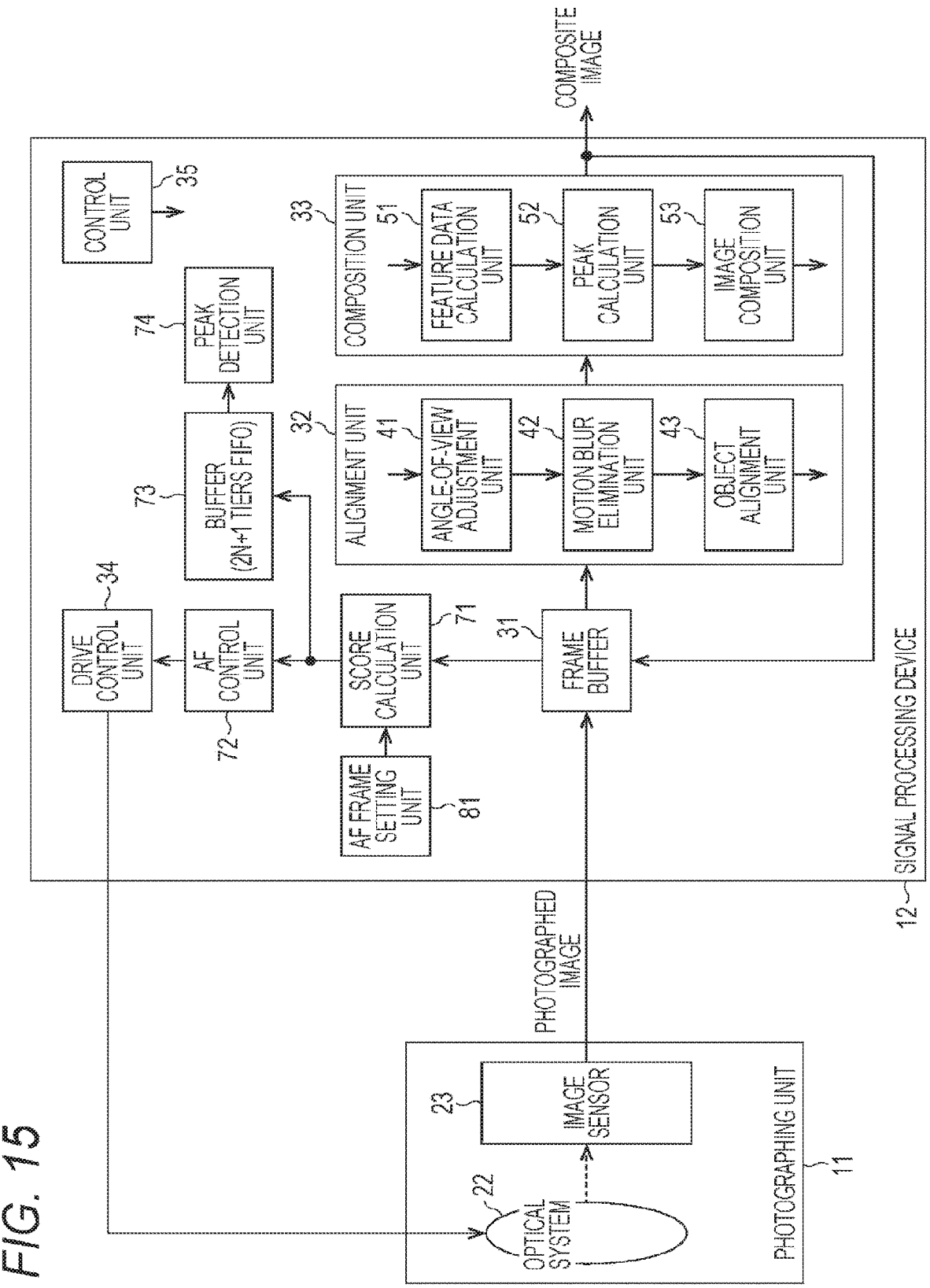
FIG. 15 is a block diagram illustrating a fourth configuration example of the signal processing device 12.

FIG. 15 is a block diagram illustrating a fourth configuration example of the signal processing device 12 in FIG. 1.

Note that in the figure, a pan corresponding to the one in FIG. 12 is assigned the same reference numeral as that in FIG. 12 to omit description of such part as appropriate.

The signal processing device 12 in FIG. 15 includes a frame buffer 31 to a control unit 35, a score calculation unit 71 to a peak detection unit 74, and an AF frame setting unit 81.

Therefore, what is common to FIG. 12 in FIG. 15 is that the signal processing device 12 includes the frame buffer 31 to the control unit 35 as well as the score calculation unit 71 to the peak detection unit 74.

The signal processing device 12 in FIG. 15 is however different from that in FIG. 12 in that the AF frame setting unit 81 is newly provided.

The signal processing device 12 in FIG. 15 has an AF function as is the case with the example in FIG. 12.

However, an AF frame is set at a predetermined position such as the center of a photographed image in the example illustrated in FIG. 12 whereas, in the example illustrated in FIG. 15, the signal processing device can set an AF frame at a position specified by a user in a photographed image.

Specifically, the AF frame setting unit 81 sets the AF frame according to an AF mode and supplies it to the score calculation unit 71.

The score calculation unit 71 calculates a focus score by using die photographed image within the AF frame supplied from the AF frame setting unit 81.

Here, the AF mode includes a normal mode and a specification mode.

The AF mode is set to the normal mode or the specification mode according to an operation of a user, for example.

In the normal mode, the AF frame setting unit 81 sets the AF frame at a default position, namely at a predetermined position such as the center of the photographed image.

In the specification mode, the AF frame setting unit 81 sets the AF frame at a position specified by the user on a photographed image according to an operation of the user.

When the user specifics a position at an edge of the photographed image, for example, the AF frame setting unit 81 sets the AF frame at the edge position.

AF Frame Setting Processing

Figure 16:
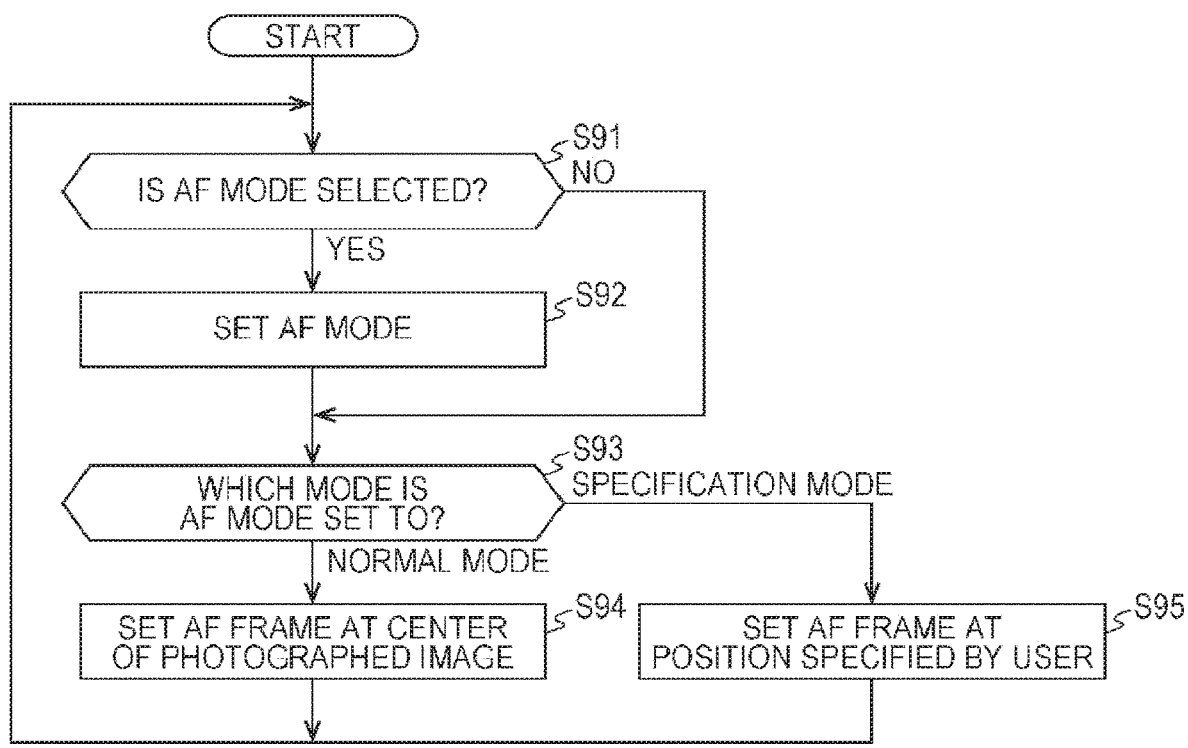
FIG. 16 is a flowchart illustrating an example of processing that sets an AF frame in the signal processing device 12.

FIG. 16 is a flowchart illustrating an example of processing that sets the AF frame in the signal processing device 12 of FIG. 15.

In step S91, the AF frame setting unit 81 determines whether a selection operation of selecting the AF mode is performed by the user.

When it is determined in step S91 that the selection operation of selecting the AF mode is performed by the user, the operation proceeds to processing in step S92, in which the AF frame setting unit 81 sets (changes) the AF mode to the normal mode or specification mode according to the selection operation by the user, then the operation proceeds to processing in step S93.

On the other hand, the operation skips the processing in step S92 and proceeds to the processing in step S93 when it is determined in step S91 that the selection operation of selecting the AF mode is not performed by the user.

In step S93, the AF frame setting unit 81 determines the (current) AF mode.

When it is determined in step S93 that the AF mode is set to the normal mode, the operation proceeds to processing in step S94, in which the AF frame setting unit 81 sets the AP frame at the center of the photographed image or the like as a default position, then the operation returns to the processing in step S91.

When it is determined in step S93 that the AF mode is set to the specification mode, the operation proceeds to processing in step S95 where the AF frame setting unit waits for the user to perform a specification operation of specifying the AF frame and sets the AF frame at a position on the photographed image specified by the specification operation, then the operation returns to the processing in step S91.

Here, the specification operation can be performed by touching the position on the photographed image displayed in a display device 13, for example.

Note that the present technology can be applied not only to an image obtained by photographing a human body but also an image obtained by photographing a living body other than the human body.

The present technology can also be applied to an image obtained by photographing an object other than the living body.

Moreover, the present technology can be applied to an arbitrary device with a photographing function other than medical equipment such as a digital camera, a vehicle-mounted image sensor, a surveillance camera installed for surveillance and security of agricultural products, and an industrial endoscope (fiberscope) system.

Furthermore, the present technology can be applied to an image photographed by a device photographing visible light as well as an image photographed by a device photographing non-visible light (electromagnetic wave).

Description of Computer to Which Present Technology is Applied

The series of processings performed by the signal processing device 12 can be implemented by hardware or software. When the series of processings are implemented by software, a program configuring the software is installed on a general-purpose computer or the like.

Now, FIG. 17 illustrates a configuration example of an embodiment of a computer installed with the program implementing the series of processings.

The program can be recorded beforehand in a hard disk 105 or a ROM 103 being a recording medium built into the computer.

Alternatively, the program can be stored (recorded) in a removable recording medium 111. The removable recording medium 111 can then be provided as so-called packaged software. Here, the removable recording medium 111 can be a flexible disk, a Compact Disc Read Only Memory (CD-ROM), a Magneto Optical (MO) disk, a Digital Versatile Disc (DVD), a magnetic disk, or a semiconductor memory, for example.

Note that the program can be installed on the computer from the removable recording medium 111 or downloaded to the computer via a communication network or broadcast network and installed on the built-in hard disk 105. Specifically, the program can be transmitted by radio from a download site to the computer via a satellite used for digital satellite broadcast or transmitted to the computer in a wired manner via a network such as a Local Area Network (LAN) or the internet, for example.

A Central Processing Unit (CPU) 102 is incorporated into the computer and connected to an input/output interface 110 through a bus 101.

When a command is input by a user operation or the like on an input unit 107 through the input/output interface 110, the CPU 102 runs a program stored in the Read Only Memory (ROM) 103 according to the command. Alternatively, the CPU 102 runs a program stored in the hard disk 105 by loading it to a Random Access Memory (RAM) 104.

The CPU 102 then performs the processing according to the aforementioned flowchart or the processing performed by the configuration illustrated in the aforementioned block diagram. Then, the CPU 102 for example outputs or transmits the processing result from an output unit 106 or a communication unit 108 through the input/output interface 110 and records the result in the hard disk 105 as needed.

Note that the input unit 107 is formed of a keyboard, a mouse, a microphone and the like. The output unit 106 is formed of a Liquid Crystal Display (LCD), a speaker and the like.

Here, in the present specification, the processing performed by the computer according to the program docs not have to be performed in time series in the order described in the flowchart. In other words, the processing performed by the computer according to the program includes processing performed in parallel or individually (such as parallel processing or processing by an object).

The program may be processed by a single computer (processor) or processed in a distributed manner by a plurality of computers. The program may also be transferred to a remote computer and run.

Moreover, in the present specification, the system refers to the assembly of a plurality of components (such as devices and modules (parts)) where it docs not matter whether or not all the components are housed in the same housing. Accordingly, a plurality of devices housed in separate housings and connected through a network as well as a device with a plurality of modules housed in a single housing are both systems.

Note that the embodiments of the present technology are not limited to the aforementioned embodiments, where various modifications can be made without departing from the scope of the present technology.

The present technology can for example employ cloud computing in which a single function is shared and processed collaboratively among a plurality of devices through a network.

Moreover, each step described in the aforementioned flowcharts can be performed by a single device or can be shared and performed by a plurality of devices.

When a single step includes a plurality of processings, the plurality of processings included in the single step can be performed by a single device or can be shared and performed by a plurality of devices.

Furthermore, the effect described in the present specification is provided by way of example and not by way of limitation, where there may be another effect.

Note that the present technology can have the following configuration.

(1)

A medical image processing apparatus including:
circuitry configured to
generate a composite image by compositing a plurality of images obtained by capturing with a medical imaging device a living body while changing a focus position, and
switch output between the generated composite image and one of the plurality of images based on a result of analysis performed on at least one of the plurality of images.

(2)

The medical image processing apparatus according to (1), wherein the circuitry is further configured to switch output between the generated composite image and one of the plurality of images based on a manual input operation.

(3)

The medical image processing apparatus according to (1)-(2), wherein the analysis performed on at least one of the plurality of images includes analysts of an angle of view adjustment.

(4)

The medical image processing apparatus according to (1)-(3), wherein the analysis performed on at least one of the plurality of images includes motion detection.

(5)

The medical image processing apparatus according to (1)-(4), wherein the analysis performed on at least one of the plurality of images includes image recognition that recognizes a treatment tool in the at least one of the plurality of images.

(6)

The medical image processing apparatus according to (1)-(5), wherein the circuitry is configured to switch the output between the generated composite image and one of the plurality of images based on the result of the analysis being lower than or equal to a predetermined threshold.

(7)

The medical image processing apparatus according to (2), wherein the manual input operation includes an input via an interface on a treatment tool.

(8)

The medical image processing apparatus according to (1)-(7), wherein the circuitry is configured to generate the composite image by selecting a pixel of a previous composite image or a pixel of a newly captured image that is in focus and compositing the previous composite image and the latest captured image.

(9)

The medical image processing apparatus according to (1)-(8), wherein the medical imaging device is configured to capture the plurality of images of the living body at an imaging frame rate, and
the circuitry is configured to output the generated composite image or the one of the plurality of images at a display frame rate, the display frame rate being equal to the imaging frame rate.

(10)

The medical image processing apparatus according to (1)-(9), wherein the circuitry is configured to output the generated composite image or the one of the plurality of images at a display frame rate, the display frame rate being at least 120 Hz.

(11)

The medical image processing apparatus according to (1)-(10), wherein the circuitry is further configured to
perform alignment between the generated composite image and a newly captured image, and
update the composite image by compositing the aligned composite image and newly captured image.

(12)

The medical image processing apparatus according to (11), wherein the circuitry is configured to adjust an angle of view of each of the generated composite image and the newly captured image and perform alignment between the generated composite image and the newly captured image after adjusting the angle of view.

(13)

The medical image processing apparatus according to (3)-(12), wherein the circuitry is configured to switch output to the one of the plurality of images when the analysis determines that a reliability of adjustment of the angle of view performed on each of the generated composite image and a newly captured image is lower than or equal to a threshold.

(14)

The medical image processing apparatus according to (11), wherein the circuitry is configured to detect motion in each of the generated composite image and the newly captured image and perform the alignment on the basis of a result of the motion detection.

(15)

The medical image processing apparatus according to (4)-(14), wherein the circuitry is configured to switch output to the one of tire plurality of images when the analysis determines that a reliability of the motion detection is lower than or equal to a threshold.

(16)

The medical image processing apparatus according to (1)-(15), wherein the plurality of images is obtained by capturing with the medical imaging device the living body while changing the focus position within a range determined based on depth information of the living body.

(17)

The medical image processing apparatus according to (1)-(16), wherein the circuitry is configured to generate the composite image by compositing the plurality of images obtained at a focus position in a predetermined range including a peak position that is a focus position at which a peak of a score, used in Auto Focus (AF), is obtained.

(18)

The medical image processing apparatus according to (1)-(17), wherein the plurality of images includes a left eye image and a right eye imago.

(19)

A medical image processing method including:
generating a composite image by compositing a plurality of images obtained by capturing with a medical imaging device a living body while changing a focus position; and
switching output between the generated composite image and one of the plurality of images based on a result of analysis performed on at least one of the plurality of images.

(20)

A medical observation system including:
a medical imaging device configured to capture a plurality of images of a living body while changing a focus position; and
circuitry configured to
generate a composite image by compositing the plurality of images captured by the medical imaging device, and
switch output between the generated composite image and one of the plurality of images based on a result of analysis performed on at least one of the plurality of images.

(21)

The medical image processing apparatus according to (20), wherein the medical imaging device is a surgical video microscope.

(22)

The medical image processing apparatus according to (20)-(21), wherein the medical imaging device is an endoscope.

(23)

The medical image processing apparatus according to (20)-(22), wherein the medical imaging device is configured to capture the plurality of images of the living body during a medical procedure.

(24)

A medical image processing apparatus including a composition unit that generates a composite image by compositing a plurality of photographed images obtained by photographing a living body while changing a focus position, and generates a latest composite image by selecting a pixel of a last composite image or a pixel of a latest photographed image that is in focus and compositing the last composite image and the latest photographed image.

(25)

The medical image processing apparatus according to (24), wherein the composition unit outputs a photographed image as the composite image when a composition restriction condition that restricts composition is satisfied.

(26)

The medical image processing apparatus according to (25), wherein the composition restriction condition is that a treatment tool photographed along with the living body in the photographed image is in motion.

(27)

The medical image processing apparatus according to (25) or (26), further including an alignment unit that performs alignment between the composite image and the photographed image, wherein the composition unit composites the composite image and the photographed image that are aligned.

(28)

The medical image processing apparatus according to (27), wherein the alignment unit adjusts an angle of view of each of the composite image and the photographed image and performs alignment between the composite image and the photographed image after adjusting the angle of view.

(29)

The medical image processing apparatus according to (28), wherein the composition restriction condition is that reliability of adjustment of the angle of view performed on each of the composite image and the photographed image is lower than or equal to a threshold.

(30)

The medical image processing apparatus according to any of (27) to (29), wherein the alignment unit detects motion in each of the composite image and the photographed image and performs the alignment on the basis of a result of the motion detection.

(31)

The medical image processing apparatus according to (30), wherein the composition restriction condition is that reliability of the motion detection is lower than or equal to a threshold.

(32)

The medical image processing apparatus according to any of (24) to (31), wherein a photographing unit that performs photographing to obtain the photographed image obtains the photographed image while changing the focus position within a range according to a user operation.

(33)

The medical image processing apparatus according to any of (24) to (31), wherein the composition unit composites a plurality of photographed images obtained at a focus position in a predetermined range including a peak position that is a focus position at which a peak of a score used in Auto Focus (AF) is obtained.

(34)

The medical image processing apparatus according to any of (24) to (33), wherein the photographing unit that performs photographing to obtain the photographed image obtains a three-dimensional (3D) photographed image.

(35)

A medical image processing method including performing composition processing that generates a composite image by compositing a plurality of photographed images obtained by photographing a living body while changing a focus position, and generates a latest composite image by selecting a pixel of a last composite image or a pixel of a latest photographed image that is in focus and compositing the last composite image and the latest photographed image.

(36)

A medical observation system including a photographing unit that photographs a living body while changing a focus position, and a composition unit that generates a composite image by compositing a plurality of photographed images photographed by the photographing unit and generates a latest composite image by selecting a pixel of a last composite image or a pixel of a Latest photographed image that is in focus and compositing the last composite image and the latest photographed image.

REFERENCE SIGNS LIST

11 Photographing unit
12 Signal processing device
13 Display device
21 Light source
22 Optical system
23 Image sensor
31 Framebuffer
32 Alignment unit
33 Composition unit
34 Drive control unit
35 Control unit
41 Angle-of-view adjustment unit
42 Motion blur elimination unit
43 Object alignment unit
51 Feature data calculation unit
52 Peak calculation unit
53 Image composition unit
61 Depth estimation unit
62 Range setting unit
63 Range storing unit
71 Score calculation unit
72 AF control unit
73 Buffer
74 Peak detection unit
81 AF frame setting unit
101 Bus
102 CPU
103 ROM
104 RAM
105 Hard disk
106 Output unit 107 Input unit
108 Communication unit
109 Drive
110 Input/output interface
111 Removable recording medium

The invention claimed is:

1. A medical image processing apparatus comprising:
circuitry configured to
obtain a plurality of medical images, each of the plurality of medical images being in focus and having a different focus depth,
generate a composite image by compositing in-focus portions of the plurality of medical images, and
switch output between the generated composite image and a selected image of the plurality of medical images, wherein the selected image satisfies a predetermined focus condition, wherein the predetermined focus condition is selected from a plurality different focus conditions.

2. The medical image processing apparatus according to claim 1, wherein the circuitry configured to switch output outputs the selected image of the plurality of medical images in case that at least one of the plurality of medical images include an unsuitable image for the compositing.

3. The medical image processing apparatus according to claim 2, wherein the unsuitable image is an image including a treatment tool.

4. The medical image processing apparatus according to claim 2, wherein the unsuitable image is an image including a motion component that exceeds a predetermined threshold.

5. The medical image processing apparatus according to claim 1, wherein the selected image of the plurality of medical images includes an object in focus.

6. The medical image processing apparatus according to claim 5, wherein the selected image of the plurality of medical images includes the object in focus at center of the image.

7. The medical image processing apparatus according to claim 1, wherein the circuitry is further configured to switch output between the generated composite image and the selected image of the plurality of medical images based on a manual input operation.

8. The medical image processing apparatus according to claim 7, wherein the manual input operation includes an input via an interface on a treatment tool.

9. The medical image processing apparatus according to claim 1, wherein the analysis performed on the at least one of the plurality of images includes analysis of an angle of view adjustment.

10. The medical image processing apparatus according to claim 1, wherein the analysis performed on the at least one of the plurality of images includes motion detection.

11. The medical image processing apparatus according to claim 1, wherein the switch output is performed based on image recognition that recognizes a treatment tool in the at least one of the plurality of images.

12. The medical image processing apparatus according to claim 1, wherein the circuitry is configured to generate the composite image by selecting a pixel of a previous composite image or a pixel of a new medical image that is in focus and compositing the previous composite image and the new medical image.

13. The medical image processing apparatus according to claim 1, wherein the circuitry is configured to output the generated composite image or the selected image of the plurality of medical images at a display frame rate, the display frame rate being equal to an imaging frame rate.

14. The medical image processing apparatus according to claim 1, wherein the circuitry is configured to output the generated composite image or the selected image of the plurality of images at a display frame rate, the display frame rate being at least 120 Hz.

15. The medical image processing apparatus according to claim 1, wherein the plurality of medical images is a plurality of endoscopic images or a plurality of microscopic images.

16. A medical image processing method comprising:
obtaining a plurality of medical images, each of the plurality of medical images being in focus and having a different focus depth, generating a composite image by compositing in-focus portions of the plurality of medical images, and
switching, based on a result of analysis performed on at least one of the plurality of medical images, output between the generated composite image and a selected image of the plurality of medical images wherein the selected image satisfies a predetermined focus condition, wherein the predetermined focus condition is selected from a plurality different focus conditions.

17. A microscopic imaging system comprising:
a microscope including an image sensor and an optical member; and
a microscope control device including circuitry configured to:
obtain a plurality of microscope images captured by the microscope, each of the plurality of microscope images being in focus and having a different focus depth,
generate a composite image by compositing in-focus portions of the plurality of microscope images, and
switch, based on a result of analysis performed on at least one of the plurality of microscope images, output between the generated composite image and a selected image of the plurality of microscope images wherein the selected image satisfies a predetermined focus condition, wherein the predetermined focus condition is selected from a plurality different focus conditions.

* * * * *